United States Patent
Cabourg et al.

(10) Patent No.: US 9,180,086 B2
(45) Date of Patent: Nov. 10, 2015

(54) PROCESS FOR TREATING STRAIGHTENED KERATIN FIBRES

(75) Inventors: Julien Cabourg, Combs la Ville (FR); Gregory Plos, Paris (FR); Laetitia Feuillette, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/122,725

(22) PCT Filed: Jun. 1, 2012

(86) PCT No.: PCT/EP2012/060354
§ 371 (c)(1),
(2), (4) Date: Mar. 7, 2014

(87) PCT Pub. No.: WO2012/164065
PCT Pub. Date: Dec. 6, 2012

(65) Prior Publication Data
US 2014/0186283 A1      Jul. 3, 2014

Related U.S. Application Data

(60) Provisional application No. 61/528,646, filed on Aug. 29, 2011, provisional application No. 61/528,689, filed on Aug. 29, 2011.

(30) Foreign Application Priority Data

Jun. 1, 2011   (FR) ..................................... 11 54802
Jun. 1, 2011   (FR) ..................................... 11 54803

(51) Int. Cl.

| | | |
|---|---|---|
| A61K 8/36 | (2006.01) |
| A61K 8/92 | (2006.01) |
| A61K 8/362 | (2006.01) |
| A61K 8/365 | (2006.01) |
| A61Q 5/04 | (2006.01) |
| A61K 8/87 | (2006.01) |
| A61K 8/44 | (2006.01) |
| A61Q 5/00 | (2006.01) |
| A61K 8/81 | (2006.01) |
| A61K 8/894 | (2006.01) |

(52) U.S. Cl.
CPC ................. *A61K 8/922* (2013.01); *A61K 8/362* (2013.01); *A61K 8/365* (2013.01); *A61K 8/44* (2013.01); *A61K 8/8117* (2013.01); *A61K 8/87* (2013.01); *A61K 8/894* (2013.01); *A61Q 5/00* (2013.01); *A61Q 5/04* (2013.01); *A61K 2800/884* (2013.01)

(58) Field of Classification Search
CPC combination set(s) only.
See application file for complete search history.

(56) References Cited

U.S. PATENT DOCUMENTS

| | | |
|---|---|---|
| 2,047,398 A | 7/1936 | Voss et al. |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,723,248 A | 11/1955 | Wright |
| 2,798,053 A | 7/1957 | Brown |
| 2,923,692 A | 2/1960 | Ackerman et al. |
| 2,961,347 A | 11/1960 | Floyd |
| 3,206,462 A | 9/1965 | McCarty |
| 3,227,615 A | 1/1966 | Korden |
| 3,579,629 A | 5/1971 | Pasero et al. |
| 3,632,559 A | 1/1972 | Matter et al. |
| 3,716,633 A | 2/1973 | Viout et al. |
| 3,770,683 A | 11/1973 | Barabas et al. |
| 3,810,977 A | 5/1974 | Levine et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,925,542 A | 12/1975 | Viout et al. |
| 3,929,735 A | 12/1975 | Barabas |
| 3,929,990 A | 12/1975 | Green et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,966,904 A | 6/1976 | Green et al. |
| 3,986,825 A | 10/1976 | Sokol |
| 3,990,459 A | 11/1976 | Papantoniou |

(Continued)

FOREIGN PATENT DOCUMENTS

| | | |
|---|---|---|
| CA | 1069522 A1 | 1/1980 |
| DE | 2330956 A1 | 1/1974 |

(Continued)

OTHER PUBLICATIONS www.folica.com/hair-101/tips-and-how-tos/how-to-flat-iron.
Accessed online Nov. 12, 2014, available online Jan. 22, 2011.*

(Continued)

*Primary Examiner* — Robert A Wax
*Assistant Examiner* — Melissa Mercier
(74) *Attorney, Agent, or Firm* — The Marbury Law Group, PLLC

(57) ABSTRACT

The present invention relates to a process for treating straightened keratin fibers, in which a composition comprising at least one carboxylic acid in its acid or salified form, at a concentration of greater than or equal to 2%, and at least one non-cellulosic polymer and/or at least one fatty substance, the pH ranging from 3 to 8, is applied to the straightened keratin fibers.

23 Claims, No Drawings

(56) References Cited

U.S. PATENT DOCUMENTS

| | | | |
|---|---|---|---|
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,075,136 A | 2/1978 | Schaper |
| 4,128,631 A | 12/1978 | Lundmark et al. |
| 4,129,711 A | 12/1978 | Viout et al. |
| 4,137,208 A | 1/1979 | Elliott |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,237,243 A | 12/1980 | Quack et al. |
| 4,240,450 A | 12/1980 | Grollier et al. |
| 4,277,581 A | 7/1981 | Vanlerberghe et al. |
| 4,282,203 A | 8/1981 | Jacquet et al. |
| 4,289,752 A | 9/1981 | Mahieu et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,390,689 A | 6/1983 | Jacquet et al. |
| 4,422,853 A | 12/1983 | Jacquet et al. |
| 4,445,521 A | 5/1984 | Grollier et al. |
| 4,509,949 A | 4/1985 | Huang et al. |
| 4,521,504 A | 6/1985 | Sakuma et al. |
| 4,579,732 A | 4/1986 | Grollier et al. |
| 4,608,250 A | 8/1986 | Jacquet et al. |
| 4,693,935 A | 9/1987 | Mazurek |
| 4,702,906 A | 10/1987 | Jacquet et al. |
| 4,719,099 A | 1/1988 | Grollier et al. |
| 4,719,282 A | 1/1988 | Nadolsky et al. |
| 4,728,571 A | 3/1988 | Clemens et al. |
| 4,777,040 A | 10/1988 | Grollier et al. |
| 4,839,166 A | 6/1989 | Grollier et al. |
| 4,948,579 A | 8/1990 | Jacquet et al. |
| 4,970,066 A | 11/1990 | Grollier et al. |
| 4,972,037 A | 11/1990 | Garbe et al. |
| 4,996,059 A | 2/1991 | Grollier et al. |
| 5,009,880 A | 4/1991 | Grollier et al. |
| 5,060,680 A * | 10/1991 | Akhtar | 132/204 |
| 5,089,252 A | 2/1992 | Grollier et al. |
| 5,089,578 A | 2/1992 | Valint et al. |
| 5,158,762 A | 10/1992 | Pierce |
| 5,196,189 A | 3/1993 | Jacquet et al. |
| 5,374,334 A | 12/1994 | Sommese et al. |
| 5,506,315 A | 4/1996 | Meyer et al. |
| 5,739,195 A | 4/1998 | Kroker et al. |
| 5,958,392 A | 9/1999 | Grollier et al. |
| 6,426,383 B1 | 7/2002 | Fong et al. |
| 6,822,039 B1 | 11/2004 | Monfreux-Gaillard et al. |
| 6,894,110 B2 | 5/2005 | Fong et al. |
| 8,449,871 B2 | 5/2013 | Mougin et al. |
| 2005/0048004 A1 | 3/2005 | de la Guardia et al. |
| 2006/0067907 A1 | 3/2006 | Mougin et al. |
| 2007/0283977 A1 | 12/2007 | Mougin et al. |

FOREIGN PATENT DOCUMENTS

| | | |
|---|---|---|
| EP | 0080976 A1 | 6/1983 |
| EP | 0122324 A1 | 10/1984 |
| EP | 0337354 A1 | 10/1989 |
| EP | 0412704 A2 | 2/1991 |
| EP | 0412707 A1 | 2/1991 |
| EP | 0582152 A2 | 2/1994 |
| EP | 0640105 A1 | 3/1995 |
| EP | 0750899 A2 | 1/1997 |
| FR | 1222944 A | 6/1960 |
| FR | 1400366 A | 5/1965 |
| FR | 1564110 A | 4/1969 |
| FR | 1580545 A | 9/1969 |
| FR | 1583363 A | 10/1969 |
| FR | 2077143 A5 | 10/1971 |
| FR | 2080759 A | 11/1971 |
| FR | 2162025 A1 | 7/1973 |
| FR | 2190406 A2 | 2/1974 |
| FR | 2252840 A1 | 6/1975 |
| FR | 2265781 A1 | 10/1975 |
| FR | 2265782 A1 | 10/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2350384 A1 | 12/1977 |
| FR | 2357241 A2 | 2/1978 |
| FR | 2368508 A2 | 5/1978 |
| FR | 2383660 A1 | 10/1978 |
| FR | 2393573 A1 | 1/1979 |
| FR | 2413907 A1 | 8/1979 |
| FR | 2416723 A1 | 9/1979 |
| FR | 2439798 A1 | 5/1980 |
| FR | 2470596 A1 | 6/1981 |
| FR | 2519863 A1 | 7/1983 |
| FR | 2598611 A1 | 11/1987 |
| FR | 2336434 A1 | 7/1997 |
| FR | 2875503 A1 | 3/2006 |
| FR | 2898603 A1 | 9/2007 |
| GB | 839805 A | 6/1960 |
| GB | 922457 A | 4/1963 |
| GB | 1021400 A | 3/1966 |
| GB | 1331819 A | 9/1973 |
| GB | 1546809 A | 5/1979 |
| GB | 1572626 A | 7/1980 |
| LU | 75370 A1 | 2/1978 |
| LU | 75371 A1 | 2/1978 |
| WO | 93/00882 A1 | 1/1993 |
| WO | 93/23009 A1 | 11/1993 |

OTHER PUBLICATIONS

Fonnum, G., et al., "Associative Thickeners, Part I: Synthesis, Reheology and Aggregation Behavior," Colloid & Polymer Science, Colloid Polym Sci. 271, 1993, pp. 380-389.

Todd, Charles, et al., "Volatile Silicone Fluids for Cosmetic Formulations," Cosmetics and Toiletries, vol. 91, Jan. 1976, pp. 29-32.

Kirk-Othmer's Encyclopedia of Chemical Technology, Third Edition, vol. 3, 1982, pp. 896-900.

Kirk-Othmer's Encyclopedia of Chemical Technology, Third Edition, vol. 15, 1982, pp. 439-458.

MacGregor, E.A., et al., "Polymers in Nature," Chapter 6, 1980, pp. 240-328.

* cited by examiner

PROCESS FOR TREATING STRAIGHTENED KERATIN FIBRES

CROSS REFERENCE TO RELATED APPLICATIONS

This is a national stage application of PCT/EP2012/060354, filed internationally on Jun. 1, 2012, which claims priority to U.S. Provisional Application Nos. 61/528,646 and 61/528,689, both filed on Aug. 29, 2011, as well as French Application Nos. FR 1154802 and 1154803, both filed on Jun. 1, 2011, all of which are incorporated herein by reference in their entireties.

The present invention relates to a process for treating keratin fibres, and in particular a process for treating straightened keratin fibres.

Two techniques are generally used to obtain permanent reshaping of the hair. They are based on breaking the —S—S— disulphide bonds present in keratin (cystine).

The first technique for permanently reshaping the hair consists, in a first stage, in opening the —S—S— disulphide bonds using a composition containing a reducing agent (reduction step), and then, after having preferably rinsed the hair, in reconstituting said disulphide bonds, in a second stage, by applying to the hair, which has been placed under tension beforehand with rollers or the like or shaped or smoothed by other means, an oxidizing composition, also known as fixative (oxidation step) so as to give the head of hair the desired shape.

This technique makes it possible, without distinction, either to wave the hair or to shape, straighten, relax or smooth it.

The second technique for obtaining permanent hair reshaping consists in performing an operation known as lanthionization, using a composition containing a base belonging to the hydroxide family. It results in disulphide bonds (—$CH_2$—S—S—$CH_2$—) being replaced with lanthionine bonds (—$CH_2$—S—$CH_2$—).

The compositions generally used for carrying out the lanthionization contain, as base, a hydroxide such as sodium hydroxide, guanidinium hydroxide or lithium hydroxide. Sodium hydroxide and guanidinium hydroxide are the main two agents used for shaping or straightening naturally frizzy hair.

Compared with the first technique previously described, using a reducing agent, this lanthionization technique does not require a fixing step since the formation of the lanthionine bridges is irreversible. It is therefore carried out in a single step. These two techniques make it possible either to wave the hair or to shape, straighten, relax or smooth it. However, the lanthionization technique is principally used for shaping naturally frizzy hair.

Treatments for long-lasting shaping of keratin fibres, and in particular hair-straightening treatments, cause considerable damage to the hair. In addition, the hair-straightening effectiveness is not always satisfactory. The hair-straightening is not perfect, the hair remains too voluminous and often exhibits frizziness that is persistent with respect to the hair-straightening treatment.

Post-treatment acid treatments are known to allow neutralization of the hair and the scalp after alkaline hair-straightening treatment.

A hair-straightening process in which a composition in the form of a mousse is applied to the straightened hair is known in particular from document US 2005/0048004, the styling mousse comprising a carboxylic acid, in particular 0.6% of glutamic acid or 0.4% of citric acid, the pH of the composition being between 3 and 8.

A hair-straightening process which comprises a step of acid rinsing of the straightened hair with a composition comprising between 0.1 and 5% by weight of an acid selected from citric acid, maleic acid, boric acid, lactic acid and phosphoric acid, between 0.1 and 5% by weight of a thickener chosen from hydroxyalkylcelluloses, between 0.1 and 10% of a wetting agent chosen from non-ionic surfactants, between 0.001 and 1% of a pH indicator and between 0.1 and 8% of laureth 23 as emulsifier, is also known from document WO09300882. The acid rinsing composition can also be applied between two applications of hair-straightening agents in order to temporarily smooth out new growth.

There is still a need to provide a process for treating keratin fibres which improves straightening of the fibre in a persistent manner and which reduces the overall volume of the hair.

The subject of the invention is therefore a process for treating straightened keratin fibres, in which a composition comprising at least one carboxylic acid in its acid or salified form, at a concentration of greater than or equal to 2%, and at least one non-cellulosic polymer and/or at least one fatty substance, the pH ranging from 3 to 8, is applied to the straightened keratin fibres.

The term "straightened keratin fibres" is intended to mean keratin fibres that have undergone a straightening, relaxing or smoothing treatment using either a reducing agent or a hydroxide. When the straightened treatment uses a reducing agent, the term "straightened keratin fibres" is intended to mean keratin fibers having undergone the whole straightened treatment, namely the reduction's step and the oxitation's step by means of an oxidizing composition (fixative). Preferably, the straightened keratin fibres of the invention are fibres that have undergone a straightening treatment with a hydroxide.

A second subject of the application is the use of a composition comprising at least one carboxylic acid in its acid or salified form for reducing hair volume.

A third subject of the application is the use of a composition comprising at least one carboxylic acid in its acid or salified form for increasing the persistence of hair-straightening.

The treatment process according to the invention makes it possible to reduce the overall volume of straightened hair, to reduce the hair mass effect, and to increase the persistence of the hair-straightening, and also makes it possible to obtain a feel without rough patches.

In the text hereinbelow, the term "at least one" is equivalent to the expression "one or more".

The composition used in the context of the process for treating straightened hair according to the invention comprises at least one carboxylic acid.

The term "carboxylic acid" is intended to mean simple carboxylic acids, polycarboxylic acids, in particular dicarboxylic acids, amino dicarboxylic acids, tricarboxylic acids, (poly)hydroxy(poly)carboxylic acids, in particular α-hydroxylated or dihydroxylated carboxylic acids, which can of course be used alone or as a mixture.

Preferably, the molecular weight of the carboxylic acid is lower than 250, better lower than 200.

As carboxylic acids that can be used in the compositions according to the invention, mention may more particularly be made of citric acid, maleic acid, succinic acid, aspartic acid, glutamic acid, lactic acid, malic acid and tartaric acid.

According to one particularly preferred embodiment of the process of the present invention, the acid used is citric acid.

The carboxylic acids used in the invention can be present in the composition, partially or totally, in the form of one of their salts.

The salts that can be used can result from the combination of the acids of the invention with an organic or inorganic, and preferably inorganic, base. Among the organic bases that may be mentioned are amines and in particular alkanolamines.

Among the inorganic bases that may be mentioned are aqueous ammonia and alkali metal or alkaline-earth metal hydroxides. Preferably, the inorganic bases are alkali metal hydroxides and even more preferentially sodium hydroxide, resulting in sodium salts.

Among the salts of these acids that may be mentioned are sodium citrate, sodium maleate, sodium succinate, sodium aspartate, sodium glutamate, sodium lactate, sodium malate and sodium tartrate.

According to one particularly preferred embodiment of the process of the present invention, the acid salt used is sodium citrate.

Preferably, the carboxylic acid(s) or carboxylic acid salt(s) are present in the composition in an amount from 2% to 50%, preferably from 2 to 10%, more preferably from 2 to 5%, the acid salt concentration being expressed in acid equivalent.

The composition used in the context of the process for treating straightened hair according to the invention may comprise at least one non-cellulosic polymer.

Preferably, the composition does not comprise any cellulosic polymer.

The term "non-cellulosic polymer" is intended to mean, for the purpose of the invention, a polymer which does not comprise a cellulose unit in its structure.

The non-cellulosic polymer may be non-ionic, anionic, cationic, amphoteric or zwitterionic.

In the composition used according to the invention, the polymer(s) may be solubilized or non-solubilized, i.e. in solid or liquid dispersion forms.

These polymers may be synthetic or natural.

They may be in the form of random polymers, in the form of block polymers, or in the form of pseudo-block polymers or gradient polymers.

The non-cellulosic polymer may be chosen from thickening polymers, fixing polymers, opacifying polymers or conditioning polymers, or from blends thereof.

The term "opacifying polymer" is intended to mean, for the purpose of the present invention, a polymer that is insoluble in the composition and that makes it possible to render the composition into which it is introduced opaque or that increases the opacity of the composition into which it is introduced. Among the opacifying polymers that may be mentioned is polystyrene in emulsion in water at 40%, in particular Modarez OS-197 from Synthron.

For the purpose of the present invention, the term "fixing polymer" is intended to mean polymers capable of giving a shape to a head of hair and/or holding the hair in a given shape. The fixing polymers are preferably anionic, non-ionic or amphoteric.

The anionic fixing polymers that can be used in the compositions according to the invention are polymers comprising groups derived from carboxylic acid, sulphonic acid or phosphoric acid and have a number-average molecular weight of between 500 and 5 000 000 approximately.

The groups derived from carboxylic acid are provided by unsaturated monocarboxylic or dicarboxylic acid monomers such as those corresponding to the formula:

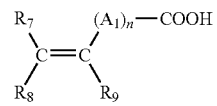

in which n is an integer from 0 to 10, $A_1$ denotes a methylene group optionally joined to the carbon atom of the unsaturated group or to the adjacent methylene group when n is greater than 1, via a heteroatom such as oxygen or sulphur, $R_7$ denotes a hydrogen atom or a phenyl or benzyl group, $R_8$ denotes a hydrogen atom or a lower alkyl or carboxyl group, and $R_9$ denotes a hydrogen atom, a lower alkyl group, or a $CH_2$—COOH, phenyl or benzyl group.

In the abovementioned formula, a lower alkyl group preferably denotes a group having 1 to 4 carbon atoms and in particular methyl and ethyl groups.

The anionic fixing polymer(s) containing carboxylic groups that are preferred according to the invention are chosen from:

A) copolymers of acrylic or methacrylic acid with a monoethylenic monomer chosen from ethylene, styrene, vinyl esters and acrylic or methacrylic acid esters, optionally grafted onto a polyalkylene glycol such as polyethylene glycol and optionally crosslinked. Such polymers are described in particular in French patent No. 1 222 944 and German patent application No. 2 330 956, the copolymers of this type comprising an optionally N-alkylated and/or hydroxyalkylated acrylamide unit in their chain as described in particular in Luxembourg patent application Nos. 75370 and 75371. Mention may also be made of copolymers of acrylic acid and of $C_1$-$C_4$ alkyl methrylate and terpolymers of vinylpyrrolidone, of acrylic acid and of $C_1$-$C_{20}$ alkyl methacrylate, for example lauryl methacrylate, such as the product sold by the company ISP under the name Acrylidone® LM and methacrylic acid/ethyl acrylate/tert-butyl acrylate terpolymers such as the product sold under the name Luvimer® 100 P by the company BASF; mention may also be made, by way of example, of methacrylic acid/acrylic acid/ethyl acrylate/methyl methacrylate copolymers in an aqueous dispersion, sold under the name Amerhold® DR 25 by the company Amerchol; in which n is an integer from 0 to 10, $A_1$ denotes a methylene group, optionally joined to the carbon atom of the unsaturated group or to the adjacent methylene group when n is greater than 1, via a heteroatom such as oxygen or sulphur, $R_7$ denotes a hydrogen atom or a phenyl or benzyl group, $R_8$ denotes a hydrogen atom or a lower alkyl or carboxyl group, and $R_9$ denotes a hydrogen atom, a lower alkyl group, or a —$CH_2$—COOH, phenyl or benzyl group.

In the abovementioned formula, a lower alkyl group preferably denotes a group having 1 to 4 carbon atoms and in particular methyl and ethyl groups.

The anionic fixing polymer(s) containing carboxylic groups that are preferred according to the invention are chosen from:

A) copolymers of acrylic or methacrylic acid with a monoethylenic monomer chosen from ethylene, styrene, vinyl esters and acrylic or methacrylic acid esters, optionally grafted onto a polyalkylene glycol such as polyethylene glycol and optionally crosslinked. Such polymers are described in particular in French patent No. 1 222 944 and German patent application No. 2 330 956, the copolymers of this type comprising an optionally N-alkylated and/or hydroxyalkylated acrylamide unit in their chain as described in particular in Luxembourg patent application Nos. 75370 and 75371. Mention may also be made of copolymers of acrylic acid and $C_1$-$C_4$ alkyl methacrylate and terpolymers of vinylpyrrolidone, acrylic acid and $C_1$-$C_{20}$ alkyl methacrylate, for example lauryl methacrylate, such as the product sold by the company ISP under the name Acrylidone® LM and methacrylic acid/ethyl acrylate/tert-butyl acrylate terpolymers such as the product sold under the name Luvimer® 100 P by the company BASF; mention may also be made, by way of example, of the methacrylic acid/acrylic acid/ethyl acrylate/methyl methacrylate copolymers in an aqueous dispersion, sold under the name Amerhold® DR 25 by the company Amerchol.

B) Crotonic acid-derived copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon-based chain, such as those containing at least 5 carbon atoms, it being possible for these polymers optionally to be grafted or crosslinked, or alternatively another vinyl, allyl or methallyl ester monomer of an α- or β-cyclic carboxylic acid; Such polymers are described, inter alia, in French patent Nos. 1 222 944, 1 580 545, 2 265 782, 2 265 781, 1 564 110 and 2 439 798. A commercial product which is part of this class is the resin 28-29-30 sold by the company National Starch.

C) Copolymers derived from $C_4$-$C_8$ monounsaturated carboxylic acids or anhydrides chosen from:
  copolymers comprising (i) one or more maleic, fumaric or itaconic acids or anhydrides and (ii) at least one monomer chosen from vinyl esters, vinyl ethers, vinyl halides, phenylvinyl derivatives, acrylic acid and its esters, the anhydride functions of these copolymers optionally being monoesterified or monoamidated. Such polymers are described, in particular, in U.S. Pat. Nos. 2,047,398, 2,723,248 and 2,102,113, and GB patent No. 839 805. Commercial products are in particular those sold under the names Gantrez® AN or ES by the company ISP;
  copolymers comprising (i) one or more maleic, citraconic or itaconic anhydride units and (ii) one or more monomers chosen from allyl or methallyl esters optionally comprising one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated;
  These polymers are described, for example, in French patent Nos. 2 350 384 and 2 357 241 of the applicant.

D) Polyacrylamides comprising carboxylate groups. The polymers comprising sulphonic groups are polymers comprising vinylsulphonic, styrenesulphonic, naphthalenesulphonic or acrylamidoalkylsulphonic units.
  These polymers can be chosen in particular from:
  salts of polyvinylsulphonic acid having a molecular weight of approximately between 1000 and 100 000, and also the copolymers of vinylsulphonic acid with an unsaturated comonomer, such as acrylic or methacrylic acids and their esters, and also acrylamide or its derivatives, vinyl ethers and vinylpyrrolidone;
  polystyrenesulphonic acid salts such as the sodium salts that are sold for example under the name Flexan® 130 by National Starch. These compounds are described in patent FR 2 198 719;
  polyacrylamidesulphonic acid salts such as those mentioned in U.S. Pat. No. 4,128,631, and more particularly polyacrylamidoethylpropanesulphonic acid;
  polyesters comprising sulphonic groups, such as the AQ resins (AQ55, AQ38 and AQ48) proposed by the company Eastman Chemical.

According to the invention, among the anionic polymers mentioned above,
the preferred polymers are copolymers of acrylic acid, such as the acrylic acid/ethyl acrylate/N-tert-butylacrylamide terpolymers sold in particular under the name Ultrahold® Strong by the company BASF, copolymers derived from crotonic acid, such as the vinyl acetate/vinyl tert-butylbenzoate/crotonic acid terpolymers proposed by the company Chimex and the crotonic acid/vinyl acetate/vinyl neododecanoate terpolymers sold in particular under the name Resin 28-29-30 by the company National Starch, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the name Gantrez® by the company ISP, the copolymers of methacrylic acid and of methyl methacrylate, the copolymers of methacrylic acid and 5 of ethyl acylate sold under the name Luvimer® MAEX or MAE by the company BASF, the vinyl acetate/crotonic acid copolymers sold under the name Luviset CA 66 by the company BASF, the vinyl acetate/crotonic acid copolymers grafted with polyethylene glycol sold under the name Aristoflex® A by the company BASF, the polymer sold under the name Fixate G-100 by the company Noveon, and polyesters comprising sulphonic groups, such as the AQ resins (AQ55, AQ38 and AQ48) proposed by the company Eastman Chemical.

Among the anionic polymers mentioned above, those which are more particularly preferred are chosen from the methyl vinyl ether/monoesterified maleic anhydride copolymers sold under the name Gantrez® ES 425 by the company ISP, the acrylic acid/ethyl acrylate/N-tert-butylacrylamide terpolymers sold under the name Ultrahold® Strong by the company BASF, the vinyl acetate/vinyl tert-butylbenzoate/crotonic acid terpolymers proposed by the company Chimex and the crotonic acid/vinyl acetate/vinyl neododecanoate terpolymers sold under the name Resin 28-29-30 by the company National Starch, the copolymers of methacrylic acid and ethyl acrylate sold under the name Luvimer® MAEX or MAE by the company BASF, the vinylpyrrolidone/acrylic acid/lauryl methacrylate terpolymers sold under the name Acrylidone® LM by the company ISP, the polymer sold under the name Fixate G-100 by the company Noveon and polyesters comprising sulphonic groups, such as the AQ resins (AQ55, AQ38 and AQ48) proposed by the company Eastman Chemical.

The non-ionic fixing polymers that may be used according to the present invention are chosen, for example, from:
  polyalkyloxazolines;
  vinyl acetate homopolymers;
  copolymers of vinyl acetate and of acrylic ester;
  copolymers of vinyl acetate and of ethylene;
  copolymers of vinyl acetate and of maleic ester, for example of dibutyl maleate;
  acrylic ester homopolymers and copolymers, for instance copolymers of alkyl acrylates and of alkyl methacrylates, such as the products sold by the company Rohm & Haas under the names Primal® AC-261 K and Eudragit® NE 30 D, by the company BASF under the name 8845, or by the company Hoechst under the name Appretan® N9212;
  copolymers of acrylonitrile and of one or more non-ionic monomers chosen, for example, from butadiene and alkyl(meth)acrylates; mention may be made of the products sold under the name CJ 0601 B by the company Rohm & Haas;

styrene homopolymers;

styrene copolymers, for instance: copolymers of styrene and of an alkyl(meth)acrylate, such as the products Mowilith® LDM 6911, Mowilith® DM 611 and Mowilith® LDM 6070 sold by the company Hoechst, and the products Rhodopas® SD 215 and Rhodopas® DS 910 sold by the company Rhodia Chimie; copolymers of styrene, of alkyl methacrylate and of alkyl acrylate; copolymers of styrene and of butadiene; or copolymers of styrene, of butadiene and of vinylpyridine;

copolymers of alkyl acetate and of urethane;

polyamides;

vinyl lactam homopolymers and copolymers.

The alkyl groups of the non-ionic polymers mentioned above preferably contain from 1 to 6 carbon atoms.

According to the present invention, the non-ionic polymers comprising vinyl lactam units (vinyl lactam homopolymers and copolymers) may be those described in the U.S. Pat. No. 3,770,683, U.S. Pat. No. 3,929,735, U.S. Pat. No. 4,521,504, U.S. Pat. No. 5,158,762 and U.S. Pat. No. 5,506,315 and in patent applications WO 94/121148, WO 96/06592 and WO 96/10593. They may be provided in pulverulent form or in the form of a solution or suspension.

The homopolymers or copolymers comprising vinyl lactam units comprise units of formula:

in which n is independently 3, 4 or 5.

The number-average molecular weight of the polymers comprising vinyl lactam units is generally greater than approximately 5000, preferably between 10,000 and 1,000,000 approximately, more preferentially between 10,000 and 100,000 approximately. Among these polymers, mention may be made of polyvinylpyrrolidones such as those sold, inter alia, under the name Luviskol® K30 and Luviskol® K90 by the company BASF; polyvinylcaprolactams such as those sold under the name Luviskol® Plus by the company BASF; poly(vinylpyrrolidone/vinyl acetate) copolymers, such as those sold under the name PVPVA® S630L by the company ISP, Luviskol® VA 73, VA 64, VA 55, VA 37 and VA 28 by the company BASF; and poly(vinylpyrrolidone/vinyl acetate/vinyl propionate) terpolymers, for instance those sold under the name Luviskol® VAP 343 by the company BASF.

The amphoteric fixing polymers that can be used in accordance with the invention can be chosen from polymers comprising units B and C distributed randomly in the polymer chain, where B denotes a unit derived from a monomer comprising at least one basic nitrogen atom and C denotes a unit derived from an acid monomer comprising one or more carboxylic or sulphonic groups, or alternatively B and C can denote groups derived from carboxybetaine or sulphobetaine zwitterionic monomers; B and C may also denote a cationic polymer chain comprising primary, secondary, tertiary or quaternary amine groups, in which at least one of the amine groups bears a carboxylic or sulphonic group connected via a hydrocarbon-based group or alternatively B and C form part of a chain of a polymer comprising an [alpha],[beta]-dicarboxylic ethylene unit in which one of the carboxylic groups has been made to react with a polyamine comprising one or more primary or secondary amine groups. The amphoteric fixing polymers corresponding to the definition given above that are more particularly preferred are chosen from the following polymers:

(1) Copolymers comprising acidic vinyl units and basic vinyl units, such as those resulting from the copolymerization of a monomer derived from a vinyl compound bearing a carboxylic group such as, more particularly, acrylic acid, methacrylic acid, maleic acid, α-chloroacrylic acid, and of a basic monomer derived from a substituted vinyl compound containing at least one basic atom, such as, more particularly, dialkylaminoalkyl methacrylate and acrylate, dialkylaminoalkylmethacrylamides and acrylamides. Such compounds are described in U.S. Pat. No. 3,836,537.

(2) Polymers comprising units derived from:

a) at least one monomer chosen from acrylamides or methacrylamides substituted on the nitrogen atom with an alkyl group, b) at least one acidic comonomer containing one or more reactive carboxylic groups, and c) at least one basic comonomer such as esters with primary, secondary, tertiary and quaternary amine substituents of acrylic and methacrylic acids and the product of quaternization of dimethylaminoethyl methacrylate with dimethyl or diethyl sulphate. The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acid or anhydride.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer, such as the products sold under the name Amphomer® or Lovocryl® 47 by the company National Starch, are particularly used.

(3) Crosslinked and acylated polyaminoamides partially or totally deriving from polyaminoamides of general formula:

(II)

in which $R_{10}$ represents a divalent group derived from a saturated dicarboxylic acid, a mono- or dicarboxylic aliphatic acid containing an ethylenic double bond, an ester of a lower alkanol having 1 to 6 carbon atoms of these acids, or a group derived from the addition of any one of said acids to a bis (primary) or bis(secondary) amine, and Z denotes a group derived from a bis(primary), mono- or bis(secondary) polyalkylene-polyamine and preferably represents:

in proportions of from 60 to 100 mol %, the group:

(III)

where x=2 and p=2 or 3, or alternatively x=3 and p=2 this group being derived from diethylenetriamine, from triethylenetetramine or from dipropylenetriamine;

in proportions of from 0 to 40 mol %, the group (III) above in which x=2 and p=1 and which is derived from ethylenediamine, or the group derived from piperazine

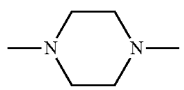

in proportions of from 0 to 20 mol %, the —NH—(CH$_2$)$_6$—NH— group being derived from hexamethylenediamine, these polyamino amides being crosslinked by addition reaction of a bifunctional crosslinking agent chosen from epihalohydrins, diepoxides, dianhydrides and bis-unsaturated derivatives, using from 0.025 to 0.35 mol of crosslinking agent per amine group of the polyamino amide and acylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the acylation are preferably propane sultone or butane sultone; the salts of the acylating agents are preferably the sodium or potassium salts.

(4) Polymers comprising zwitterionic units of formula:

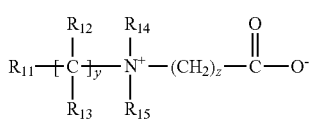

(IV)

in which $R_{11}$ denotes a polymerizable unsaturated group such as an acrylate, methacrylate, acrylamide or methacrylamide group, y and z represent an integer from 1 to 3, $R_{12}$ and $R_{13}$ represent a hydrogen atom, or a methyl, ethyl or propyl group, $R_{14}$ and $R_{15}$ represent a hydrogen atom or an alkyl group such that the sum of the carbon atoms in $R_{14}$ and $R_{15}$ does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate.

By way of example, mention may be made of methyl methacrylate/methyl dimethylcarboxymethylammonioethyl methacrylate copolymers such as the product sold under the name Diaformer Z301 by Sandoz.

(5) Polymers derived from chitosan comprising monomer units corresponding to the following formulae:

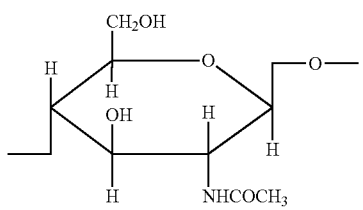

(D)

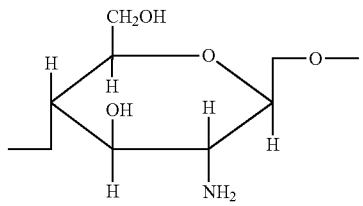

(E)

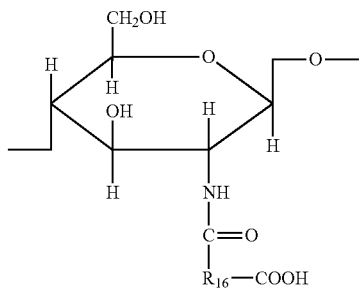

(F)

the unit (D) being present in proportions of between 0 and 30%, the unit (E) in proportions of between 5% and 50% and the unit (F) in proportions of between 30% and 90%, it being understood that, in this unit (F), $R_{16}$ represents a group of formula:

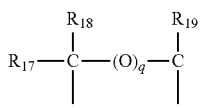

in which, if q=0, $R_{17}$, $R_{18}$ and $R_{19}$, which may be identical or different, each represent a hydrogen atom, a methyl, hydroxyl, acetoxy or amino residue, a monoalkylamine residue or a dialkylamine residue that are optionally interspersed with one or more nitrogen atoms and/or optionally substituted with one or more amine, hydroxyl, carboxyl, alkylthio or sulphonic groups, or an alkylthio residue in which the alkyl group bears an amino residue, at least one of the groups $R_{17}$, $R_{18}$ and $R_{19}$ being, in this case, a hydrogen atom;

or, if q=1, $R_{17}$, $R_{18}$ and $R_{19}$ each represent a hydrogen atom, and also the salts formed by these compounds with bases or acids.

(6) Polymers with units corresponding to the general formula (V) are described, for example, in French patent 1 400 366:

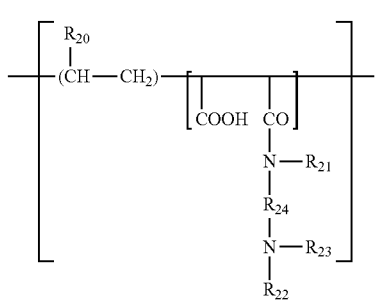

(V)

in which $R_{20}$ represents a hydrogen atom, a CH$_3$O, CH$_3$CH$_2$O or phenyl group, $R_{21}$ denotes a hydrogen atom or a lower alkyl group such as methyl or ethyl, $R_{22}$ denotes a hydrogen atom or a $C_1$-$C_6$ lower alkyl group such as methyl or ethyl, $R_{23}$ denotes a $C_1$-$C_6$ lower alkyl group such as methyl or ethyl or a group corresponding to the formula: —$R_{24}$—N($R_{22}$)2, $R_{24}$ representing a —$CH_2$—$CH_2$—, —$CH_2$—$CH_2$—$CH_2$— or —$CH_2$—$CH(CH_3)$— group, $R_{22}$ having the meanings mentioned above.

(7) Polymers derived from the N-carboxyalkylation of chitosan, such as N-carboxymethylchitosan or N-carboxybutylchitosan sold under the name Evalsan by the company Jan Dekker.

(8) Amphoteric polymers of the type -D-X-D-X chosen from:
a) polymers obtained by the action of chloroacetic acid or sodium chloroacetate on compounds comprising at least one unit of formula:

-D-X-D-X-D- (VI)

where D denotes a group

and X denotes the symbol E or E', E or E', which may be identical or different, denote a divalent group that is an alkylene group with a straight or branched chain containing up to 7 carbon atoms in the main chain, which is unsubstituted or substituted with hydroxyl groups and which can comprise, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;

b) polymers of formula:

-D-X-D-X- (VII)

where D denotes a group

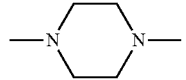

and X denotes the symbol E or E' and at least once E'; E having the meaning given above and E' is a divalent group that is an alkylene group with a straight or branched chain having up to 7 carbon atoms in the main chain, which is unsubstituted or substituted with one or more hydroxyl groups and containing one or more nitrogen atoms, the nitrogen atom being substituted with an alkyl chain that is optionally interspersed by an oxygen atom and necessarily comprising one or more carboxyl functions or one or more hydroxyl functions and betainized by reaction with chloroacetic acid or sodium chloroacetate.

(9) ($C_1$-$C_5$)Alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric fixing polymers mentioned above, the ones that are most particularly preferred according to the invention are those of class (3), such as the copolymers whose CTFA name is Octylacrylamide/acrylates/butylaminoethyl methacrylate copolymer, such as the products sold under the names Amphomer®, Amphomer® LV 71 or Lovocryl® 47 by the company National Starch and those of class (4) such as the methyl methacrylate/methyl dimethylcarboxymethylammonioethyl methacrylate copolymers, sold, for example, under the name Diaformer Z301 by the company Sandoz.

The fixing polymers may also be chosen from optionally siliconized anionic or non-ionic polyurethanes. By way of polymers of polyurethane type, mention may be made of the polymers Luviset Pur et Luviset Si Pur sold by the company BASF.

According to the invention, it is also possible to use anionic or non-ionic polymers of grafted silicone type comprising a polysiloxane portion and a portion consisting of a non-silicone organic chain, one of the two portions constituting the main chain of the polymer, and the other being grafted onto said main chain.

These polymers are described, for example, in patent applications EP-A-0 412 704, EP-A-0 412 707, EP-A-0 640 105 and WO 95/00578, EP-A-0 582 152 and WO 93/23009 and U.S. Pat. No. 4,693,935, U.S. Pat. No. 4,728,571 and U.S. Pat. No. 4,972,037.

Other examples of grafted silicone polymers are, in particular, polydimethylsiloxanes (PDMSs) onto which are grafted, via a thiopropylene-type connecting chain, mixed polymer units of the poly(meth)acrylic acid type and of the poly(alkyl(meth)acrylate) type, and polydimethylsiloxanes (PDMSs) onto which are grafted, via a thiopropylene-type connecting chain, polymer units of the poly(isobutyl(meth) acrylate) type. As other type of non-polyurethane silicone polymers, mention may be made of the product Luviflex® Silk sold by the company BASF; and the products VS 70 et VS 80 sold by the company 3M.

For the purpose of the present invention, the term "conditioning polymer" is intended to mean a polymer which makes it possible to improve the cosmetic condition of keratin fibres, in particular in terms of ease of disentangling and of softness to the touch.

The conditioning polymers are preferably cationic polymers.

The cationic polymer(s) that may be used in accordance with the present invention may be chosen from all of those already known per se to enhance the cosmetic properties of hair treated with detergent compositions, these being, in particular, the polymers described in patent application EP-A-0 337 354 and in French patent applications FR-A-2 270 846, FR-A-2 383 660, FR-A-2 598 611, FR-A-2 470 596, FR-A-2 519 863 and FR-A-2 875 503.

The preferred cationic polymer(s) is (are) chosen from those that contain in their structure units comprising primary, secondary, tertiary and/or quaternary amine groups that may for example either form part of the main polymer chain or be borne by a side substituent directly attached thereto.

Among the cationic polymers that may be mentioned more particularly are polymers of the polyamine, polyaminoamide and polyquaternary ammonium type. Among these polymers, mention may be made of:

(1) Homopolymers or copolymers derived from acrylic or methacrylic esters or amides, which are crosslinked or non-crosslinked, and comprising at least one of the units having the following formula (I), (II), (Ill) or (IV):

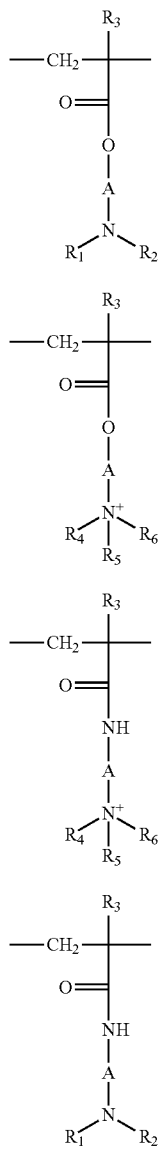

in which:

R₁ and R₂, which are identical or different, each represent a hydrogen atom or an alkyl group having from 1 to 6 carbon atoms, and preferably a methyl or ethyl group;

R₃, identical or different, at each occurrence denotes a hydrogen atom or a CH₃ group;

A, identical or different, at each occurrence represents a linear or branched alkyl group of 1 to 6 carbon atoms, preferably 2 or 3 carbon atoms, or a hydroxyalkyl group of 1 to 4 carbon atoms;

R₄, R₅ and R₆, which are identical or different, each represent an alkyl group having from 1 to 6 carbon atoms or a benzyl group, and preferably an alkyl group having from 1 to 6 carbon atoms.

The polymers of family (1) can also contain one or more unit(s) derived from comonomers that may be chosen from the family of acrylamides, methacrylamides, diacetone acrylamides, acrylamides and methacrylamides substituted on the nitrogen with lower (C₁-C₄) alkyls, acrylic or methacrylic acids or esters thereof, vinyl lactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulphate or with a dimethyl halide, such as the product sold under the name Hercofloc by the company Hercules, copolymers of acrylamide and of methacryloyloxyethyltrimethylammonium chloride which are described, for example, in patent application EP-A-080976 and are sold under the name Bina Quat P 100 by the company Ciba Geigy, the copolymer of acrylamide and of methacryloyloxyethyltrimethylammonium methosulphate sold under the name Reten by the company Hercules, quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, and crosslinked polymers of methacryloyloxy(C₁-C₄)alkyltri (C₁-C₄)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, particularly methylenebisacrylamide. A crosslinked acrylamide/methacryloyloxyethyltrimethylammonium chloride copolymer (20/80 by weight) in the form of a dispersion containing 50% by weight of said copolymer in mineral oil can more particularly be used. This dispersion is sold under the name Salcare® SC 92 by the company Ciba. Use may also be made of a crosslinked homopolymer of methacryloyloxyethyltrimethylammonium chloride containing approximately 50% by weight of the homopolymer in mineral oil or in a liquid ester. These dispersions are sold under the names Salcare® SC 95 and Salcare® SC 96 by the company Ciba.

(2) Non-cellulosic cationic polysaccharides, in particular chosen from guar gums containing trialkylmmonium cationic groups. Use is made, for example, of guar gums modified with a 2,3-epoxypropyltrimethylammonium salt (for example, chloride).

Such products are sold in particular under the trade names Jaguar C13 S, Jaguar C 15, Jaguar C 17 or Jaguar C162 by the company Meyhall.

(3) Polymers formed from piperazinyl units and divalent alkylene or hydroxyalkylene radicals containing straight or branched chains, optionally interrupted with oxygen, sulphur or nitrogen atoms or with aromatic or heterocyclic rings, and also the oxidation and/or quaternization products of these polymers. Such polymers are described in particular in French patents 2 162 025 and 2 280 361.

(4) Water-soluble cationic polyaminoamides, prepared in particular by polycondensation of an acid compound with a polyamine; these polyaminoamides may be crosslinked with an epihalohydrin, a diepoxide, a dianhydride, an unsaturated dianhydride, a bis-unsaturated derivative, a bis-halohydrin, a bis-azetidinium, a bis-haloacyldiamine or a bis-alkyl halide or else with an oligomer resulting from the reaction of a bifunctional compound which is reactive towards a bis-halohydrin, a bis-azetidinium, a bis-haloacyldiamine, a bis-alkyl halide, an epihalohydrin, a diepoxide or a bis-unsaturated derivative; these polyaminoamides may be alkylated, or quaternized if they contain one or more tertiary amine functions. Such polymers are described in particular in French patents 2 252 840 and 2 368 508.

(5) Polyaminoamide derivatives resulting from the condensation of polyalkylene polyamines with polycarboxylic acids followed by alkylation with bifunctional agents. Mention may be made, for example, of adipic acid/dialkylaminohydroxyalkyldialkylenetriamine polymers in which the alkyl group comprises from 1 to 4 carbon atoms and preferably denotes methyl, ethyl or propyl. Such polymers are in particular described in French patent 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reaction of a polyalkylene polyamine containing two primary amine groups and at least one secondary amine group with a dicarboxylic acid chosen from diglycolic acid and saturated aliphatic dicarboxylic acids having from 3 to 6 carbon atoms. The mole ratio between the polyalkylene polyamine and the dicarboxylic acid is between 0.8:1 and 1.4:1; the polyaminoamide resulting therefrom is reacted with epichlorohydrin in a mole ratio of epichlorohydrin relative to the secondary amine group of the polyaminoamide of between 0.5:1 and 1.8:1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(7) Alkyldiallylamine or dialkyldiallylammonium cyclopolymers, such as the homopolymers or copolymers containing, as the main constituent of the chain, units corresponding to formula (V) or (VI):

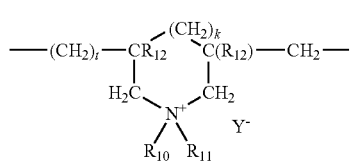

(V)

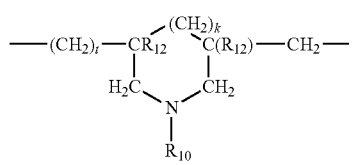

(VI)

in which k and t are equal to 0 or 1, the sum k+t being equal to 1; $R_{12}$ denotes a hydrogen atom or a methyl group; $R_{10}$ and $R_{11}$ each, independently of one another, denote an alkyl group having from 1 to 6 carbon atoms, a hydroxyalkyl group in which the alkyl group has preferably 1 to 5 carbon atoms, a lower amidoalkyl group (i.e. the alkyl part of which is $C_1$-$C_4$), or else $R_{10}$ and $R_{11}$ may denote, together with the nitrogen atom to which they are attached, a heterocyclic group, such as piperidinyl or morpholinyl; $Y^-$ is an anion such as bromide, chloride, acetate, borate, citrate, tartrate, bisulphate, bisulphite, sulphate or phosphate. These polymers are in particular described in French patent 2 080 759 and in its Certificate of Addition 2 190 406.

$R_{10}$ and $R_{11}$ each, independently of one another, preferably denote an alkyl group containing from 1 to 4 carbon atoms.

Among the polymers defined above, mention may be made of dialkyldiallylammonium chloride homopolymers, more particularly dimethyldiallylammonium chloride homopolymer (INCI name: Polyquaternium-6) sold under the name Merquat® 100 by the company Nalco (and homologues thereof of low weight-average molecular weights) and dialkyldiallylammonium chloride copolymers, more particularly the copolymer of dimethyldiallylammonium chloride and of acrylamide sold under the name Merquat® 550.

(8) Diquaternary ammonium polymers containing repeating units corresponding to formula (VII):

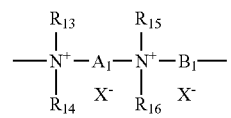

(VII)

in which:

$R_{13}$, $R_{14}$, $R_{15}$ and $R_{16}$, which are identical or different, represent aliphatic, alicyclic or arylaliphatic groups containing from 1 to 20 carbon atoms, or lower hydroxyalkylaliphatic groups (i.e. the alkyl part of which is $C_1$-$C_4$), or else $R_{13}$, $R_{14}$, $R_{15}$ and $R_{16}$, together or separately, constitute, with the nitrogen atoms to which they are attached, heterocycles optionally containing a second heteroatom other than the nitrogen, or else $R_{13}$, $R_{14}$, $R_{15}$ and $R_{16}$ each represent a linear or branched $C_1$-$C_6$ alkyl group substituted with a nitrile, ester, acyl, amide or CO—O—$R_{17}$-E or —CO—NH—$R_{17}$-E group in which $R_{17}$ is an alkylene group and E is a quaternary ammonium group;

$A_1$ and $B_1$ represent polymethylene groups containing from 2 to 20 carbon atoms, which may be linear or branched and saturated or unsaturated and may contain, bonded to or intercalated in the main chain, one or more aromatic rings, or one or more oxygen or sulphur atoms, or sulphoxide, sulphone, disulphide, amino, alkylamino, hydroxyl, quaternary ammonium, ureido, amide or ester groups, and $X^-$ denotes an anion derived from a mineral or organic acid;

$A_1$, $R_{13}$ and $R_{15}$ may form, with the two nitrogen atoms to which they are attached, a piperazine ring; moreover, if $A_1$ denotes a saturated or unsaturated, linear or branched alkylene or hydroxyalkylene group, $B_1$ may also denote a group:

—$(CH_2)_n$—CO-E'-OC—$(CH_2)_n$— in which n denotes an integer from 0 to 7 and E' denotes:

a) a glycol residue of formula —O—Z—O—, in which Z denotes a linear or branched hydrocarbon-based group, or a group corresponding to one of the following formulae:

$-(CH_2-CH_2-O)_x-CH_2-CH_2-$ $-[CH_2-CH(CH_3)-O]_y-CH_2-CH(CH_3)-$ in which x and y each denote an integer from 1 to 4, representing a defined and unique degree of polymerization or any number from 1 to 4 representing an average degree of polymerization;
b) a bis-secondary diamine residue such as a piperazine derivative;
c) a bis-primary diamine residue of formula $-NH-Y-NH-$, in which Y denotes a linear or branched hydrocarbon-based group, or else the divalent group $-CH_2-CH_2-S-S-CH_2-CH_2$;
d) a ureylene group of formula $-NH-CO-NH-$.

Preferably, $X^-$ is an anion such as chloride or bromide.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of the polymers which consist of repeating units corresponding to formula (VIII):

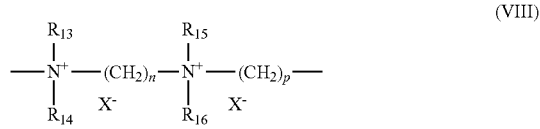

in which $R_{13}$, $R_{14}$, $R_{15}$ and $R_{16}$, which are identical or different, each denote an alkyl or hydroxyalkyl group having from 1 to 4 carbon atoms approximately, n and p are integers ranging from 2 to 20 approximately, and $X^-$ is an anion derived from an organic or mineral acid. Preferably, $R_{13}$, $R_{14}$, $R_{15}$ and $R_{16}$ each denote a methyl group. As an example of a polymer that may be used corresponding to formula (VIII), mention may be made of hexadimethrine chloride, sold under the name Mexomer PO by the company Chimex.
(9) Polyquaternary ammonium polymers consisting of units of formula (IX):

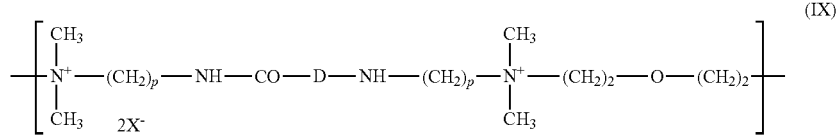

in which:
p denotes an integer ranging from 1 to 6 approximately,
D may be nothing or may represent a group
$-(CH_2)_r-CO-$ in which r denotes a number equal to 4 or 7, and
$X^-$ denotes an anion derived from a mineral or organic acid.

Cationic polymers comprising units of formula (IX) are in particular described in patent application EP-A-122 324 and may be prepared according to the processes described in U.S. Pat. Nos. 4,157,388, 4,390,689, 4,702,906 and 4,719,282.

Among these polymers, the ones that are preferred are those with a molecular weight, measured by carbon-13 NMR, of less than 100 000, and that have the formula (IX) in which:
p is equal to 3, and
a) D represents a group $-(CH_2)_4-CO-$, X denotes a chlorine atom, the molecular weight measured by carbon-13 NMR ($^{13}C$ NMR) being approximately 5600; a polymer of this type is sold by the company Miranol under the name Mirapol-AD1,
b) D represents a group $-(CH_2)_7-CO-$, X denotes a chlorine atom, the molecular weight measured by carbon-13 NMR ($^{13}C$ NMR) being approximately 8100; a polymer of this type is sold by the company Miranol under the name Mirapol-AZ1,
c) D denotes the value zero, X denotes a chlorine atom, the molecular weight measured by carbon-13 NMR ($^{13}C$ NMR) being approximately 25 500; a polymer of this type is sold by the company Miranol under the name Mirapol-A15,
d) a "block copolymer" formed from units corresponding to the polymers described in paragraphs a) and c), sold by the company Miranol under the names Mirapol-9 ($^{13}C$ NMR molecular weight of approximately 7800), Mirapol-175 ($^{13}C$ NMR molecular weight of approximately 8000) and Mirapol-95 ($^{13}C$ NMR molecular weight of approximately 12 500).

Even more particularly, the polymer containing units of formula (IX) in which p is equal to 3, D denotes the value zero and X denotes a chlorine atom, the molecular weight measured by carbon-13 NMR ($^{13}C$ NMR) being approximately 25 500, is preferred according to the invention.
(10) Quaternary polymers of vinylpyrrolidone and of vinylimidazole, for instance the products sold under the names Luviquat FC 905, FC 550 and FC 370 by the company BASF.
(11) Cationic polyamines such as Polyquart H sold by Henkel, referred to under the name polyethylene glycol (15) tallow polyamine in the CTFA dictionary.
(12) Vinylamide homopolymers or copolymers and in particular partially hydrolysed vinylamide homopolymers such as poly(vinylamine/vinylamide)s. These polymers are formed from at least one vinylamide monomer corresponding to the following formula:

$H_2C=CR_2NRC(O)R_1$ in which R, $R_1$ and $R_2$ are each chosen from a hydrogen atom, a $C_1$-$C_{20}$ alkyl group, an aryl group and an alkylaryl group in which the alkyl part comprises from 1 to 20 carbon atoms.

In particular, said monomer may be chosen from N-vinylformamide, N-methyl-N-vinylacetamide and N-vinylacetamide. Preferably, poly(vinylamine/N-vinylformamide) is used, as sold under the name Catiofast VMP by the company BASF or under the name Lupamin 9030 by the company BASF.

These polymers may be formed, for example, by radical polymerization of a vinylamide monomer followed by partial acidic or basic hydrolysis of the amide functions to quaternizable amine functions, as described in patent applications WO 2007/005 577, U.S. Pat. No. 5,374,334, U.S. Pat. No. 6,426,383 and U.S. Pat. No. 6,894,110.

(13) Cationic polyurethanes consisting essentially:

(a1) of at least one cationic unit derived from at least one tertiary or quaternary amine bearing at least two reactive functions containing labile hydrogen, (a2) of at least one non-ionic unit derived from at least one polyolefin bearing at least two reactive functions containing labile hydrogen, said polyolefin comprising at least 10 mol % of units comprising at least one C=C (carbon-carbon) double bond, relative to the total units forming said polyolefin;

(b) of at least one unit derived from a compound comprising at least two isocyanate functions.

This type of polymer preferably has an elastic nature; what is meant by this is that said polymer is a macromolecular material which returns rapidly to its initial shape and its initial dimensions once a weak stress that produced a considerable deformation has ceased.

These polymers can be obtained by polycondensation of compounds bearing reactive functions containing labile hydrogen with compounds comprising at least two isocyanate functions.

The expression "reactive functions containing labile hydrogen" is intended to mean functions which are capable, after the departure of a hydrogen atom, of forming covalent bonds with the isocyanate functions of compounds comprising at least two isocyanate functions. By way of example of such functions, mention may be made of hydroxyl, primary amine or secondary amine groups, or else thiol groups. Depend group on the nature of the reactive functions bearing the labile hydrogen (—OH, —NH$_2$, —NHR or —SH), the polycondensation results in, respectively, polyurethanes, polyureas or polythiourethanes. Thus, the polymers that can be used in the compositions according to the invention may be urethane/urea and/or thiourethane copolymers. All these polymers are grouped together in the present application, in the interests of simplification, under the term polyurethanes.

The cationic polyurethane(s) that can be used in the composition according to the invention therefore comprise at least one cationic unit (a1) resulting from at least one tertiary or quaternary amine bearing at least two reactive functions containing labile hydrogen.

The tertiary amine is preferably protonatable at a pH selected between pH 1 and pH 12. The term "protonatable" is intended to mean that said tertiary amine function can be at least partially neutralized with a neutralizing agent or with a function of the medium in which it is formulated.

When the tertiary or quaternary amines forming the units (a1) bear more than two functions containing labile hydrogen, the polyurethanes obtained have a branched structure.

However, the tertiary or quaternary amines forming the units (a1) preferably bear only two reactive functions containing labile hydrogen and the polyurethanes obtained by polycondensation consequently have an essentially linear structure.

It is of course also possible to use a mixture of bifunctional amines optionally containing a low proportion of amines bearing more than two reactive functions containing labile hydrogen.

The tertiary or quaternary amines forming the cationic units (a1) are preferably chosen from the compounds corresponding to one or more of the following formulae:

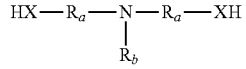

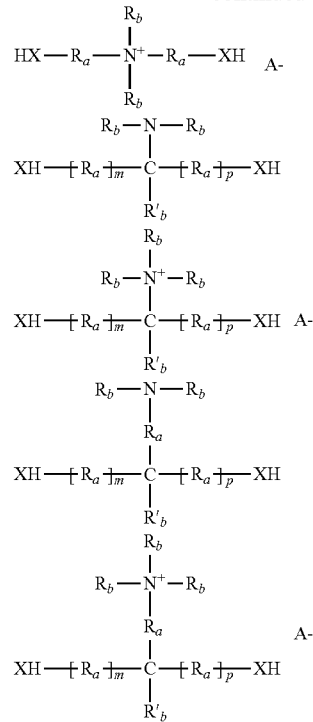

in which:

each $R_a$, independently of one another, represents a linear or branched $C_1$-$C_6$ alkylene or else $C_3$-$C_6$ cycloalkylene or arylene divalent group, or mixtures thereof; it being possible for these groups to be substituted with one or more halogen atoms and/or to comprise one or more heteroatoms chosen from O, N, P and S, each $R_b$, independently of one another, represents a linear or branched $C_1$-$C_6$ alkyl or else $C_3$-$C_6$ cycloalkyl or else aryl group, or mixtures thereof; it being possible for these groups to be substituted with one or more halogen atoms and/or to comprise one or more heteroatoms chosen from O, N, P and S, each $R'_b$ represents a hydrogen atom or a linear or branched $C_1$-$C_6$ alkyl or else $C_3$-$C_6$ cycloalkyl or else aryl group, or mixtures thereof; it being possible for these groups to be substituted with one or more halogen atoms and/or to comprise one or more heteroatoms chosen from O, N, P and S, m and p are, independently of one another, equal to 0 or 1; preferably m=1 and p=1, each X represents, independently of one another, an oxygen or sulphur atom or an NH or NRc group, in which Rc represents a $C_1$-$C_6$ alkyl group, and A$^-$ represents a physiologically acceptable counterion, and in particular a halide such as chloride or bromide.

Preferably, the amines are chosen from compounds corresponding to one or more of the formulae:

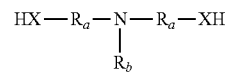 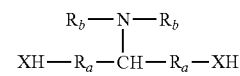

$$R_b-N-R_b$$
$$|$$
$$R_a$$
$$|$$
$$XH-R_a-CH-R_a-XH$$

in which:
- $R_a$ is a linear or branched $C_1$-$C_6$ alkylene divalent group, in particular a methylene or ethylene group; and/or
- $R_b$ is a linear or branched $C_1$-$C_6$ alkyl group, in particular a methyl, ethyl, n-butyl, isobutyl or tert-butyl group; and/or
- X denotes an oxygen atom.

Even more preferentially, the amines have the formula:

$$HO-R_a-N-R_a-OH$$
$$|$$
$$R_b$$

in which $R_a$ is a linear or branched $C_1$-$C_6$ alkylene divalent group, in particular a methylene or ethylene group; and $R_b$ is a linear or branched $C_1$-$C_6$ alkyl group, in particular a methyl, ethyl, n-butyl, isobutyl or tert-butyl group.

By way of tertiary amines that are particularly preferred, mention may be made of N-methyldiethanolamine and N-tert-butyldiethanolamine.

The protonatable tertiary amines can be totally or partially neutralized with a neutralizing agent, such as an organic acid comprising at least one carboxylic, sulphonic and/or phosphoric acid function or with a mineral acid. By way of example of preferred acids, mention may be made of hydrochloric acid, sulphuric acid, acetic acid, propionic acid, citric acid, gluconic acid, tartaric acid, lactic acid, phosphoric acid, benzoic acid, stearic acid, oleic acid, 2-ethylcaproic acid, behenic acid, betaine hydrochloride, and mixtures thereof.

The cationic polyurethane(s) that can be used in the composition according to the invention also comprise at least one non-ionic unit (a2) resulting from at least one polyolefin bearing at least two reactive functions containing labile hydrogen, said polyolefin comprising at least 10 mol % of units comprising at least one (residual) C=C double bond, relative to the total units forming said polyolefin. Preferably, the polyolefin(s) is (are) non-ionic.

Preferably, the reactive functions containing labile hydrogen are located at the ends of the polyolefin. In particular, said reactive functions containing labile hydrogen are hydroxides. Preferentially, the number of hydroxide units is close to, or even equal to 2

Again preferably, the polyolefin(s) forming the unit (a2) is (are) chosen from homopolymers and/or copolymers of olefins, bearing at their ends reactive functions containing labile hydrogen and having a glass transition temperature (Tg), measured by differential scanning calorimetry (DSC) according to standard ASTM D3418-97, of less than 10° C.

The polyurethane(s) in the composition according to the invention can comprise several units (a2) resulting from several polyolefins, which are identical or different (mixtures of polyolefins); however, in this case, each of the polyolefins comprises at least 10 mol % of units comprising at least one C=C double bond.

The term "unit comprising a C=C double bond" is intended to mean a unit which comprises at least one residual C=C double bond, preferably a single double bond; it may, for example, be a unit resulting from the polymerization of a butadiene or isoprene unit, all isomeric forms included (cis or trans, 1, 2 or 1,4).

The polyolefin that can be used may be an olefin homopolymer. Mention may, for example, be made of homopolymers of 1,2-butadiene, of 1,4-butadiene or of isoprene, and in particular:

1,4-polybutadienes, in their cis and trans forms:

$$(-CH_2-\overset{H}{\underset{|}{C}}=\overset{H}{\underset{|}{C}}-CH_2-)_n$$

1,2-polybutadienes:

$$-[CH_2-CH(CH=CH_2)-]_n$$

poly(cis-1,4-isoprene)s:

$$(-CH_2-\overset{H}{\underset{|}{C}}=\overset{CH_3}{\underset{|}{C}}-CH_2-)_n$$

poly(trans-1,4-isoprene)s:

$$(-CH_2-\overset{H}{\underset{|}{C}}=\underset{\underset{CH_3}{|}}{C}-CH_2-)_n$$

The polyolefin that can be used may also be a copolymer of different olefins (olefin copolymer), with the proviso that the final polyolefin comprises at least 10 mol % of units comprising at least one C=C double bond.

In a first embodiment, said polyolefin may consist exclusively of units comprising at least one C=C double bond. Mention may, for example, be made of copolymers, in particular random copolymers, comprising 1,2-butadiene units and/or 1,4-butadiene units in the cis and trans forms thereof, and/or isoprene units, in particular cis-1,4-isoprene and trans-1,4-isoprene units, as a mixture. Mention may in particular be made of (1,2-butadiene/1,4-butadiene) random copolymers.

Preferably, the polyolefin(s) that can be used may be random polyolefin(s) and have hydroxyl end groups and correspond to the following structure:

$$HO-(X)_{x'}-[(\cdots)_m(\cdots)_p(\cdots)_q]_n-(X)_{x'}-OH$$

in which:
m, p and q are mole fractions ranging from 0 to 1, and m+p+q=1; with in particular m ranging from 0.1 to 0.8, or even from 0.15 to 0.7; p ranging from 0.1 to 0.8, or even from 0.15 to 0.7; and q ranging from 0.05 to 0.5, or even from 0.1 to 0.4;
n is an integer ranging from 10 to 100 and in particular from 15 to 50;
x'=0 or 1, and
X represents a divalent carbon-based group, in particular a linear, cyclic or branched alkylene group comprising from 1 to 10 carbon atoms; such as, for example, a methylene, ethylene, propylene or isopropylene group.

They can preferably have a number-average molecular weight, Mn, ranging from 400 to 50 000, preferably from 500 to 30 000, in particular from 1000 to 15 000 and better still from 1500 to 12 000.

More particularly, mention may be made of:
polybutadienes with hydroxyl end groups, such as the polymers having the structure:

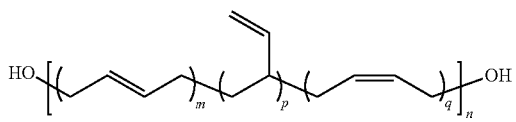

with m=0.6, p=0.2 and q=0.2 (mole fractions) and n=25.

Mention may in particular be made of the commercial products Poly bd R20LM and Poly bd R45HTLO from Sartomer;
polybutadienes with primary hydroxyl end groups, such as the polymers that may be represented by the following structure:

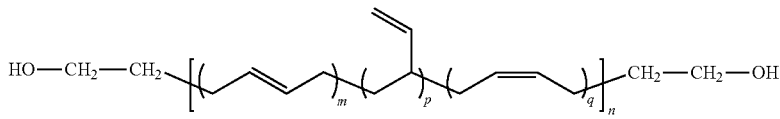

which are random copolymers, in particular of 1,4-cis-butadiene and of 1,4-trans-butadiene with m=0.17, p=0.65 and q=018 (mole fractions) and n is such that the number-average molecular weight Mn ranges from 1000 to 10 000, in particular from 2000 to 6000 (g·mol$^{-1}$).

Mention may in particular be made of the commercial products Krasol LBH-P 2000, 3000 or 5000 from Sartomer;
polybutadienes with secondary hydroxyl end groups, such as the polymers that may be represented by the following structure:

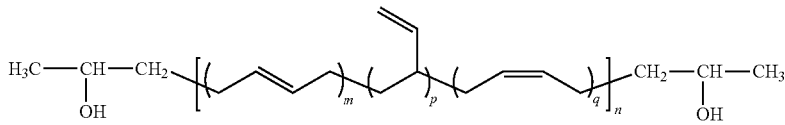

which are random copolymers of 1,4-cis-butadiene and of 1,4-trans-butadiene with m=0.17, p=0.65 and q=0.18 (mole fractions) and n is such that the number-average molecular weight Mn ranges from 1000 to 12 000, in particular from 2000 to 10 000 (g·mol$^{-1}$).

Mention may in particular be made of the commercial products Krasol LBH 2000, 3000, 5000 or 10000 from Sartomer.

In a second embodiment, said polyolefin(s) can also comprise additional units which do not comprise a C=C double bond.

However, these additional units are present in a maximum amount of 90 mol % given that the final polyolefin must comprise at least 10 mol % of units comprising at least one C=C double bond.

These additional olefin units can in particular be chosen from ethylene —(CH$_2$—CH$_2$)$_n$—, propylene —(CH$_2$—CH$_2$)$_n$— or isopropylene —(CH$_2$CH(CH$_3$))$_n$— units, and/or butylene units of formula:

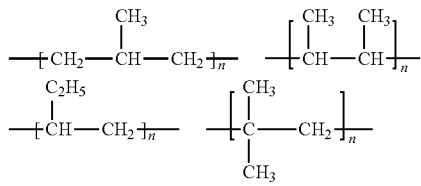

and mixtures thereof.

The olefin homopolymers or copolymers as defined above may undergo, after polymerization, a partial hydrogenation of the residual double bonds. This hydrogenation cannot in any way be total.

Indeed, the polyolefin(s) that may be used to form the units (a2) according to the invention must necessarily comprise at least 10 mol % of units comprising at least one (residual) C=C double bond, relative to the total units forming said polyolefin.

They preferably comprise at least 20 mol %, in particular at least 40 mol %, or even at least 50 mol %, preferentially at least 80 mol %, and more particularly 100 mol %, of units comprising at least one C=C double bond, in particular comprising just one C=C double bond.

This content of units comprising at least one C=C double bond can in particular be determined by the usual techniques, in particular by NMR or by iodine assay. Preferably, the polyolefin(s) that can be used to form the non-ionic units (a2) have a number-average molecular weight (Mn) ranging from 400 to 50 000, preferably from 500 to 30 000, in particular from 1000 to 15 000, and even better still from 1500 to 12 000.

Preferably, the polyolefin(s) that can be used in the context of the invention is (are):
homopolymers such as 1,4-polybutadiene and 1,2-polybutadiene;
copolymers of structure:

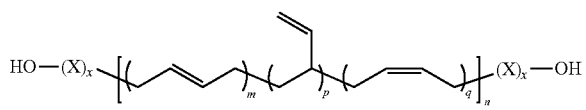

in which:
m, p and q are mole fractions ranging from 0 to 1, and m+p+q=1; with in particular m ranging from 0.1 to 0.8, or even from 0.15 to 0.7; p ranging from 0.1 to 0.8, or even from 0.15 to 0.7; and q ranging from 0.05 to 0.5, or even from 0.1 to 0.4;

n is an integer ranging from 10 to 100 and in particular from 15 to 50;

x=0 or 1, and

X represents a divalent carbon-based group, in particular a linear, cyclic or branched alkylene group comprising from 1 to 10 carbon atoms; such as, for example, a methylene, ethylene, propylene or isopropylene group.

The cationic polyurethane(s) that can be used in the composition according to the invention also comprise(s) at least one unit (b) resulting from at least one compound bearing at least two isocyanate functions.

It may of course be a mixture of several compounds comprising at least two isocyanate functions.

The compounds comprising at least two isocyanate functions can be chosen from diisocyanates, or mixtures of a diisocyanate and a polyisocyanate comprising more than two isocyanate functions, said polyisocyanate preferably representing 0.1% to 40% by weight of said mixture, in particular 0.5% to 35%, or even 1% to 30% by weight, of said mixture.

The compounds comprising at least two isocyanate functions can preferably be chosen from conjugated or non-conjugated, aromatic or non-aromatic cyclic aliphatic diisocyanates. They may in particular be chosen from methylenediphenyl diisocyanate, methylenecyclohexane diisocyanate, isophorone diisocyanate, toluene diisocyanate, naphthalene diisocyanate, 1,4-butane diisocyanate and 1,6-hexane diisocyanate, and a mixture thereof; preferably isophorone diisocyanate. Preferentially, the polyurethane(s) that can be used in the composition according to the invention consist(s) essentially:

of at least one cationic unit resulting from amines of formula:

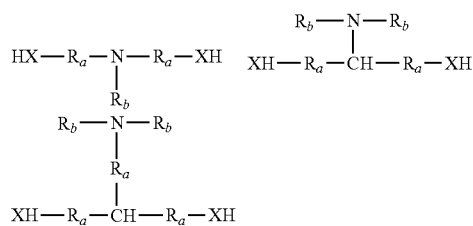

in which:
$R_a$ is a linear or branched $C_1$-$C_6$ alkylene divalent group, in particular a methylene or ethylene group;
$R_b$ is a linear or branched $C_1$-$C_6$ alkyl group, in particular a methyl, ethyl, n-butyl, isobutyl or tert-butyl group;
and X represents a hydrogen atom;
with at least one non-ionic unit resulting from polyolefins chosen from 1,4-polybutadiene and 1,2-polybutadiene homopolymers; or the copolymers of structure:

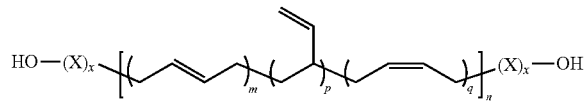

in which:
m, p and q are mole fractions ranging from 0 to 1, and m+p+q=1; with in particular m ranging from 0.1 to 0.8, or even from 0.15 to 0.7; p ranging from 0.1 to 0.8, or even from 0.15 to 0.7; and q ranging from 0.05 to 0.5, or even from 0.1 to 0.4;

n is an integer ranging from 10 to 100 and in particular from 15 to 50;

x=0 or 1, and

X represents a divalent carbon-based group, in particular a linear, cyclic or branched alkylene group comprising from 1 to 10 carbon atoms; such as, for example, a methylene, ethylene, propylene or isopropylene group;
of at least one unit resulting from aliphatic diisocyanates.

Even more preferentially, the polyurethane(s) that can be used according to the invention consist(s) essentially:

of at least one cationic unit resulting from amines of formula:

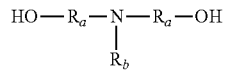

in which $R_a$ is a linear or branched $C_1$-$C_6$ alkylene divalent group, in particular a methylene or ethylene group; and $R_b$ is a linear or branched $C_1$-$C_6$ alkyl group, in particular a methyl, ethyl, n-butyl, isobutyl or tert-butyl group:
and more particularly of at least one cationic unit chosen from N-methyldiethanolamine and N-tert-butyldiethanolamine;
of at least one non-ionic unit resulting from polyolefins of structure:

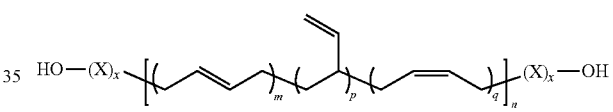

in which:
m, p and q are mole fractions ranging from 0 to 1, and m+p+q=1; with in particular m ranging from 0.1 to 0.8, or even from 0.15 to 0.7; p ranging from 0.1 to 0.8, or even from 0.15 to 0.7; and q ranging from 0.05 to 0.5, or even from 0.1 to 0.4;

n is an integer ranging from 10 to 100 and in particular from 15 to 50;

x=0 or 1, and

X represents a divalent carbon-based group, in particular a linear, cyclic or branched alkylene group comprising from 1 to 10 carbon atoms; such as, for example, a methylene, ethylene, propylene or isopropylene group;
of at least one unit resulting from diisocyanates chosen from methylenecyclohexane diisocyanate, isophorone diisocyanate, 1,4-butane diisocyanate and 1,6-hexane diisocyanate; preferably isophorone diisocyanate.

The polyurethanes that can be used according to the invention consist essentially of units (a1), (a2) and (b) as defined above, which implies that they do not comprise any additional units other than these units.

Among all the polyurethanes mentioned above, use is preferably made of the polyurethanes formed by the following monomers:
(a1) at least one N-methyldiethanolamine (denoted by NMDEA),
(a2) at least one ethylene/butylene non-ionic copolymer as sold under the name Krasol LBH-P 2000, and
(b) at least one isophorone diisocyanate (noted IPDI).

Preferably, the amines forming the cationic units (a1) represent from 0.1% to 50%, in particular from 1% to 30% and even better still from 5% to 20% by weight, relative to the total weight of the final polyurethane.

Preferably, the polyolefins forming the non-ionic units (a2) represent from 30% to 99% by weight, in particular from 50% to 90%, and even better still from 60% to 80% by weight, relative to the total weight of final polyurethane.

Preferably, the compounds comprising at least two isocyanate functions, forming the units (b), are present in an essentially stoichiometric amount relative to the sum of the tertiary/quaternary amines forming the units (a1) and the polyolefins forming units (a2).

Preferably, the compounds comprising at least two isocyanate functions, forming the units (b), represent from 1% to 60% by weight, in particular from 5% to 50% by weight, and better still from 15% to 35% by weight, relative to the total weight of the final polyurethane.

More preferably, the polyurethanes according to the invention are formed from:
  20 to 55 mol %, in particular from 25 to 50 mol %, or even from 30 to 47 mol % of tertiary or quaternary amine capable of forming the units (a1);
  1 to 30 mol %, in particular from 2 to 25 mol %, or even from 3 to 20 mol % of polyolefin capable of forming the units (a2);
  30 to 65 mol %, in particular 35 to 60 mol %, or even 45 to 55 mol % and of compound comprising at least two isocyanate functions capable of forming the units (b).

Preferentially, the mole ratio between (b) and (a1) and (a2) is close to 1.

These polyurethanes and the syntheses thereof are described, for example, in patent application FR-A-2 898 603.

(14) Other cationic polymers that may be used in the context of the invention are cationic proteins or cationic protein hydrolysates, polyalkyleneimines, in particular polyethyleneimines, polymers containing vinylpyridine or vinylpyridinium units, and chitin derivatives.

The conditioning polymers are preferably chosen from the families (1), (2), (7) and (8).

For the purpose of the present invention, the term "thickening polymer" is intended to mean a polymer which, when introduced at 1% in a pure aqueous solution or an aqueous-alcoholic solution containing 30% ethanol, and at pH 7, makes it possible to achieve a viscosity of at least 100 cps and preferably of at least 500 cps, at 25° C. and at a shear rate of 1 s$^{-1}$. This viscosity may be measured using a cone/plate viscometer (Haake R600 rheometer or the like). Preferably, these polymers increase, through their presence, the viscosity of the compositions into which they are introduced by at least 50 cps and preferably 200 cps, at 25° C. and a shear rate of 1 s$^{-1}$.

The non-cellulosic thickening polymers may be ionic or non-ionic, associative or non-associative polymers, of natural or synthetic origin.

The non-associative thickening polymers are thickening polymers not containing a $C_{10}$-$C_{30}$ fatty chain.

The aqueous-phase-thickening non-associative non-cellulosic polymers are especially chosen from:
(i) homopolymers and copolymers containing ethylenically unsaturated monomers,
(ii) vinylpyrrolidone homopolymers or copolymers,
(iii) non-cellulosic polysaccharides.

The purely synthetic thickening polymers according to the invention are advantageously acrylic and/or methacrylic acid polymers or copolymers, for instance acrylic acid/ethyl acrylate copolymers and carboxyvinyl polymers. Examples of such polymers or copolymers are in particular the "Carbomer" products (CTFA) sold by the company Goodrich under the name Carbopol (Carbopol 980, 981, 954, 2984, 5984) or Synthalen or the polyglyceryl methacrylate sold by the company Guardian under the name Lubragel or the polyglyceryl acrylate sold under the name Hispagel by the company Hispano Chimica.

Polyethylene glycols (PEGs) and derivatives thereof may also be used as thickener.

The following may also advantageously be used as thickener:
  crosslinked 2-acrylamido-2-methylpropanesulphonic homopolymers and copolymers,
  optionally crosslinked acrylamide and ammonium acrylate copolymers,
  optionally crosslinked methacryloyloxyethyltrimethylammonium chloride homopolymers and copolymers,
  optionally crosslinked, partially or totally neutralized copolymers of acrylamide and of 2-acrylamido-2-methylpropanesulphonic acid.

As crosslinked acrylamide/ammonium acrylate copolymers used in accordance with the present invention, mention may be made more particularly of acrylamide/ammonium acrylate copolymers (5/95 by weight) crosslinked with a polyolefinically unsaturated crosslinking agent, such as divinylbenzene, tetraallyloxyethane, methylenebisacrylamide, diallyl ether, polyallyl polyglyceryl ethers or allyl alcohol ethers of the sugar series, such as erythritol, pentaerythritol, arabitol, mannitol, sorbitol or glucose.

Similar copolymers are described and prepared in French patent FR 2 416 723 and U.S. Pat. No. 2,798,053 and U.S. Pat. No. 2,923,692.

This type of crosslinked copolymer is in particular used in the form of a water-in-oil emulsion. Such an emulsion is sold under the name Bozepol C by the company Hoechst.

The copolymers of acrylamide and 2-acrylamido-2-methylpropanesulphonic acid used in accordance with the present invention are copolymers crosslinked with a polyolefinically unsaturated compound, such as those mentioned previously, and partially or totally neutralized with a neutralizer such as sodium hydroxide, potassium hydroxide, aqueous ammonia or an amine such as triethanolamine or monoethanolamine.

These particular copolymers are incorporated into the compositions of the invention, preferentially, in the form of water-in-oil emulsions. Such an emulsion is sold under the name Sepigel 305 by the company SEPPIC.

The crosslinked copolymer of acrylamide and of methacryloyloxyethyltrimethylammonium chloride used according to the invention is more particularly a copolymer obtained by copolymerization of acrylamide and of dimethylaminoethyl methacrylate quaternized with methyl chloride, followed by crosslinking with an olefinically unsaturated compound, in particular methylenebisacrylamide. A crosslinked acrylamide/methacryloyloxyethyltrimethylammonium chloride copolymer (about 50/50 by weight) in the form of a dispersion is more particularly used. This dispersion is sold under the name Salcare SC92 by the company Ciba.

A crosslinked methacryloyloxyethyltrimethylammonium chloride homopolymer preferably in the form of an inverse dispersion may be used. These dispersions are in particular sold under the names Salcare SC95 and Salcare SC96 by the company Ciba.

The non-crosslinked copolymers of methacrylamide and of a methacryloyloxyethyltrimethylammonium halide such as methacryloyloxyethyltrimethylammonium chloride are, for example, the products sold under the trade names Rohagit KF 400 and KF 720 by the company Rohm & Haas.

Among the homopolymers or copolymers containing ethylenically unsaturated monomers of ester and/or amide type that may be mentioned are polyamides, in particular the products sold under the names: Cyanamer P250 by the company Cytec (polyacrylamide); methyl methacrylate/ethylene glycol dimethacrylate copolymers (PMMA MBX-8C by the company US Cosmetics); butyl methacrylate/methyl methacrylate copolymers (Acryloid B66 by the company Rohm & Haas); polymethyl methacrylate (BPA 500 by the company Kobo).

The vinylpyrrolidone homopolymers or copolymers are chosen in particular from crosslinked vinylpyrrolidone homopolymers such as the Polymer ACP-10 sold by ISP.

The thickening polysaccharides are in particular chosen from glucans, modified or unmodified starches (such as those derived, for example, from cereals, for instance wheat, corn or rice, from vegetables, for instance yellow pea, and tubers, for instance potato or cassava), amylose, amylopectin, glycogen, dextrans, mannans, xylans, arabans, galactans, galacturonans, chitin, chitosans, glucuronoxylans, arabinoxylans, xyloglucans, glucomannans, pectic acids and pectins, arabinogalactans, carrageenans, agars, gum arabics, gum tragacanths, ghatti gums, karaya gums, carob gums, galactomannans such as guar gums and non-ionic derivatives thereof (hydroxypropyl guar), and mixtures thereof.

In general, the compounds of this type that may be used in the present invention are chosen from those described in particular in Kirk-Othmer's *Encyclopedia of Chemical Technology*, Third Edition, 1982, volume 3, pp. 896-900, and volume 15, pp. 439-458, in *Polymers in Nature* by E. A. MacGregor and C. T. Greenwood, published by John Wiley & Sons, Chapter 6, pp. 240-328, 1980, and in *Industrial Gums—Polysaccharides and their Derivatives*, edited by Roy L. Whistler, Second Edition, published by Academic Press Inc., the content of these three publications being entirely included in the present patent application by way of reference.

Starches and guar gums, and derivatives thereof, will preferably be used.

The polysaccharides may be modified or unmodified.

The unmodified guar gums are, for example, the products sold under the name Vidogum GH 175 by the company Unipectine and under the names Meypro-Guar 50 and Jaguar C by the company Rhodia Chimie.

The modified non-ionic guar gums are in particular modified with $C_1$-$C_6$ (poly)hydroxyalkyl groups.

Among the hydroxyalkyl groups that may be mentioned, for example, are hydroxymethyl, hydroxyethyl, hydroxypropyl and hydroxybutyl groups.

These guar gums are well known in the prior art and can be prepared, for example, by reacting the corresponding alkene oxides such as, for example, propylene oxides, with the guar gum so as to obtain a guar gum modified with hydroxypropyl groups.

The degree of (poly)hydroxyalkylation, which corresponds to the number of alkylene oxide molecules consumed by the number of free hydroxyl functions present on the guar gum, preferably ranges from 0.4 to 1.2.

Such non-ionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhodia Chimie or under the name Galactasol 4H4FD2 by the company Aqualon, or the product Guardel D15 sold by the company Lubrizol.

Mention will also be made of carboxymethylhydroxypropyl guars, neutralized at their point of electron neutrality, for example in an acidic medium with hydrochloric acid, citric acid or lactic acid, or a mixture, such as the products Benaqua 1000 sold by the company Elementis.

Mention will also be made of carboxylated carrageenens, neutralized at their point of electron neutrality, for example in an acidic medium with hydrochloric acid, citric acid or lactic acid, or a mixture, such as the products Satiagum UTC 10, Satiagum UTC 30, Satiagel UME 614 and Satiagel UTC 508 from the company Cargill, and Nutricol GP 312 and Gelcarin PC 379 from the company FMC Biopolymer.

Mention will also be made of non-ionic carrageenans, such as the product Aquagel sold by the company Ikeda.

Mention will also be made of xanthan gums, neutralized at their point of electron neutrality, for example in an acidic medium with hydrochloric acid, citric acid or lactic acid, or a mixture, such as the products Rhodicare XC and Rhodicare CFT from the company Rhodia, Keltrol CG-T, Keltrol CG and Keltrol CG-BT from the company CP Kelco, and Nomcort Z from the company Nisshin Oillio.

Among the thickening polymers used in the invention, mention may be made of non-cellulosic associative polymers that are well known to those skilled in the art and in particular of non-ionic, anionic, cationic or amphoteric nature.

It is recalled that "associative polymers" are polymers that are capable, in an aqueous medium, of reversibly associating with each other or with other molecules.

Their chemical structure more particularly comprises at least one hydrophilic region and at least one hydrophobic region.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the associative polymers of anionic type that may be mentioned are:

those comprising at least one hydrophilic unit and at least one fatty-chain allyl ether unit, more particularly those whose hydrophilic unit is formed by an ethylenic unsaturated anionic monomer, even more particularly by a vinylcarboxylic acid and most particularly by an acrylic acid or a methacrylic acid or mixtures thereof.

Among these anionic associative polymers, those that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl(meth) acrylate, divinylbenzene, (poly)ethylene glycol dimethacrylate and methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), in particular those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);

those comprising i) at least one hydrophilic unit of unsaturated olefinic carboxylic acid type, and ii) at least one hydrophobic unit of the type such as a ($C_{10}$-$C_{30}$) alkyl ester of an unsaturated carboxylic acid.

($C_{10}$-$C_{30}$)alkyl esters of unsaturated carboxylic acids that are useful in the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. No. 3,915,921 and U.S. Pat. No. 4,509,949.

By way of example, mention may be made of the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

Mention may also be made of the acrylic acid/lauryl methacrylate/vinylpyrrolidone terpolymer sold under the name Acrylidone LM by the company ISP, and Aculyn 22® sold by the company Rohm and Haas, which is an oxyalkylenated methacrylic acid/ethyl acrylate/stearyl methacrylate terpolymer.

More particularly, only its partially or totally neutralized forms will thus be used.

For the AMPS® Polymers of AMPS® (2-acrylamido-2-methylpropanesulphonic acid), in particular random amphiphilic polymers of AMPS® modified by reaction with a $C_6$-$C_{22}$ n-monoalkylmine or di-n-monoalkylamine, and such as those described in patent application WO 00/31154. The preferred polymers of this family are chosen from amphiphilic copolymers of AMPS® and of at least one ethylenically unsaturated hydrophobic monomer.

Use may also be made of copolymers, which may or may not be crosslinked and which may or may not be neutralized, comprising from 15 to 60% by weight of AMPS® units and from 40 to 85% by weight of ($C_8$-$C_{16}$)alkyl(meth)acrylamide units or of ($C_8$-$C_{16}$)alkyl(meth)acrylate units with respect to the polymer, such as those described in application EP-A750 899;

terpolymers comprising from 10 mol % to 90 mol % of acrylamide units, from 0.1 mol % to 10 mol % of AMPS® units and from 5 mol % to 80 mol % of n-($C_6$-$C_{18}$)alkylacrylamide units, such as those described in U.S. Pat. No. 5,089,578.

Mention may also be made of copolymers of totally neutralized AMPS® and of dodecyl methacrylate, and also crosslinked and non-crosslinked copolymers of AMPS® and of n-dodecylmethacrylamide, such as those described in the Morishima articles mentioned above.

Among the cationic associative polymers, mention may be made of cationic associative polyurethanes, the compound sold by the company Noveon under the name Aqua CC and which corresponds to the INCI name Polyacrylate-1 Crosspolymer.

Polyacrylate-1 Crosspolymer is the product of polymerization of a monomer mixture comprising:

a di($C_1$-$C_4$ alkyl)amino($C_1$-$C_6$ alkyl) methacrylate,
one or more $C_1$-$C_{30}$ alkyl esters of (meth)acrylic acid,
a polyethoxylated $C_{10}$-$C_{30}$ alkyl methacrylate (20-25 mol of ethylene oxide units),
a 30/5 polyethylene glycol/polypropylene glycol allyl ether,
a hydroxy($C_2$-$C_6$ alkyl) methacrylate, and
an ethylene glycol dimethacrylate.

Mention may also be made of cationic poly(vinyllactam) polymers. Such polymers are described, for example, in patent application WO-00/68282. As cationic poly(vinyllactam) polymers according to the invention, vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, vinylpyrrolidone/dimethylaminopropylmethacrylamide/lauryldimethylmethacrylamidopropylammonium tosylate or chloride terpolymers are used in particular.

The amphoteric associative polymers are preferably chosen from those comprising at least one non-cyclic cationic unit. Even more particularly, the ones that are preferred are those prepared from or comprising 1 to 20 mol %, preferably 1.5 to 15 mol % and even more particularly 1.5 to 6 mol % of fatty-chain monomer relative to the total number of moles of monomers. Amphoteric associative polymers according to the invention are described and prepared, for example, in patent application WO 98/44012. Among the amphoteric associative polymers according to the invention, the ones that are preferred are acrylic acid/(meth)acrylamidopropyltrimethylammonium chloride/stearyl methacrylate terpolymers.

The associative polymers of non-ionic type that may be used according to the invention are preferably chosen from:

(a) copolymers of vinylpyrrolidone and of fatty-chain hydrophobic monomers, of which examples that may be mentioned include:

the products Antaron V216® or Ganex V216® (vinylpyrrolidone/hexadecene copolymer) sold by the company I.S.P., the products Antaron V220® or Ganex V220® (vinylpyrrolidone/eicosene copolymer) sold by the company I.S.P., (b) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®, (c) copolymers of hydrophilic methacrylates or acrylates and of hydrophobic monomers comprising at least one fatty chain, for instance the polyethylene glycol methacrylate/lauryl methacrylate copolymer, (d) polyurethane polyethers comprising in their chain both hydrophilic blocks usually of polyoxyethylenated nature and hydrophobic blocks, which may be aliphatic sequences alone and/or cycloaliphatic and/or aromatic sequences, (e) polymers with an aminoplast ether backbone containing at least one fatty chain, such as the Pure Thix® compounds sold by the company Sud-Chemie, (f) associative guar derivatives, for instance hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be envisaged. In addition, the polymer may comprise a hydrocarbon-based chain at one end or at both ends of a hydrophilic block.

The polyurethane polyethers may be multiblock, in particular in triblock form. The hydrophobic blocks may be at each end of the chain (for example: triblock copolymer containing a hydrophilic central block) or distributed both at the ends and in the chain (for example multiblock copolymer). These same polymers may also be graft polymers or star polymers.

The non-ionic fatty-chain polyurethane polyethers may be triblock copolymers in which the hydrophilic block is a polyoxyethylenated chain comprising from 50 to 1000 oxyethylene groups. The non-ionic polyurethane polyethers comprise a urethane bond between the hydrophilic blocks, whence arises the name.

By extension, also included among the non-ionic fatty-chain polyurethane polyethers are those in which the hydrophilic blocks are linked to the lipophilic blocks via other chemical bonds.

As examples of non-ionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane bond, sold at a solids content of 20% in water, may also be used.

It is also possible to use solutions or dispersions of these polymers, in particular in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

Mention will also be made of the polyoxyethylenated polyurethane polyether comprising an alpha, omega stearyl end group Rheolate FX 1100 sold by the company Elementis. By way of example, mention may be made of the polymer Dermothix 100 sold by the company Alzo, which is a molecule comprising two oxyethylene units, each linked to a $C_{18}$ hydrocarbon-based group at the end of the chain and linked to one another via a polyurethane block.

The polyurethane polyethers that may be used according to the invention are in particular those described in the article by G. Formum, J. Bakke and Fk. Hansen—Colloid Polym. Sci 271, 380.389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold in particular by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Preferably, the polymers of the invention are chosen from homopolymers and copolymers containing ethylenically unsaturated monomers, non-cellulosic polysaccharides such as guar gums or xanthan gums, which are optionally modified, and polyurethanes.

Preferably, the compositions of the invention contain at least one thickening polymer and/or at least one opacifying polymer. Even more preferentially, the compositions of the invention contain at least one thickening polymer.

When it comprises non-cellulosic polymer, the composition comprises from 0.01 to 50% by weight of one or more non-cellulosic polymers, preferably from 0.5 to 10%, preferably from 1% to 5%, relative to the total weight of the composition.

The composition used in the context of the process for treating straightened hair according to the invention may comprise one or more fatty substances.

For the purpose of the present invention, the term "fatty substance" is intended to mean an organic compound which is insoluble in water at normal temperature (25° C.) and at atmospheric pressure (760 mmHg, i.e. $1.013 \times 10^5$ Pa), that is to say with a solubility of less than 4% by weight, preferably of less than 1% by weight and even more preferentially of less than 0.1% by weight. They have in their structure at least one hydrocarbon-based chain comprising at least 6 carbon atoms or a sequence of at least two siloxane groups. In addition, the fatty substances are soluble in organic solvents under the same temperature and pressure conditions, for instance chloroform, ethanol or benzene. The fatty substances of the invention are not oxyalkylenated.

Preferably, the fatty substance may be chosen from hydrocarbons, fatty alcohols, fatty esters, silicones, fatty acids and fatty ethers, or mixtures thereof.

The fatty substances of the invention may be liquid or non-liquid at ambient temperature (25° C.) and at atmospheric pressure (760 mmHg; i.e. $1.013 \times 10^5$ Pa).

The liquid fatty substances of the invention preferably have a viscosity of less than or equal to 2 Pa·s, better still less than or equal to 1 Pa·s and even better still less than or equal to 0.1 Pa·s at a temperature of 25° C. and at a shear rate of 1 $s^{-1}$.

The term "liquid hydrocarbon" is intended to mean a hydrocarbon composed solely of carbon and hydrogen atoms, which is liquid at normal temperature (25° C.) and at atmospheric pressure (760 mmHg; i.e. $1.013 \times 10^5$ Pa).

More particularly, the liquid hydrocarbons are chosen from:
  linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane.
  linear or branched hydrocarbons of mineral, animal or synthetic origin, containing more than 16 carbon atoms, such as liquid paraffins, liquid petroleum jelly, polydecenes, hydrogenated polyisobutene such as Parleam®, and squalane.

In one preferred variant, the liquid hydrocarbon(s) is (are) chosen from liquid paraffins and liquid petroleum jelly.

The term "liquid fatty alcohol" is intended to mean a non-glycerolated and non-oxyalkylenated fatty alcohol that is liquid at normal temperature (25° C.) and at atmospheric pressure (760 mmHg; i.e. $1.013 \times 10^5$ Pa).

Preferably, the liquid fatty alcohols of the invention comprise from 8 to 30 carbon atoms.

The liquid fatty alcohols of the invention may be saturated or unsaturated.

The saturated liquid fatty alcohols are preferably branched. They may optionally comprise in their structures at least one aromatic or non-aromatic ring. They are preferably acyclic.

More particularly, the saturated liquid fatty alcohols of the invention are chosen from octyldodecanol, isostearyl alcohol and 2-hexyldecanol. Octyldodecanol is most particularly preferred. These unsaturated liquid fatty alcohols exhibit in their structures at least one double or triple bond. When several double bonds are present, there are preferably 2 or 3 of them, and they may be conjugated or unconjugated. These unsaturated fatty alcohols may be linear or branched. They may optionally comprise in their structure at least one aromatic or non-aromatic ring. They are preferably acyclic.

More particularly, the unsaturated liquid fatty alcohols of the invention are chosen from oleyl alcohol, linoleyl alcohol, linolenyl alcohol and undecylenyl alcohol. Oleyl alcohol is most particularly preferred.

The term "liquid fatty ester" is intended to mean an ester derived from a fatty acid and/or from a fatty alcohol and that is liquid at normal temperature (25° C.) and at atmospheric pressure (760 mmHg; i.e. $1.013 \times 10^5$ Pa).

The esters are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the invention are derived is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate. Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used. Mention may in particular be made of: diethyl sebacate; diisopropyl sebacate; bis(2-ethylhexyl)sebacate; diisopropyl adipate; di-n-propyl adipate; dioctyl adipate; bis(2-ethylhexyl)adipate; diisostearyl adipate; bis(2-ethylhexyl)maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; and diethylene glycol diisononanoate. The composition may also comprise, as liquid fatty ester, sugar esters and diesters of $C_6$-$C_{30}$ and preferably $C_{12}$-$C_{22}$ fatty acids. It is recalled that the term "sugar" is intended to mean oxygen-bearing hydrocarbon-based compounds which contain several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and in particular sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

Finally, natural or synthetic esters of mono-, di- or triacids with glycerol may also be used.

Among these, mention may be made of plant oils.

As oils of plant origin or synthetic triglycerides that may be used in the composition of the invention as liquid fatty esters, examples that may be mentioned include:

triglyceride oils of plant or synthetic origin, such as liquid fatty acid triglycerides comprising from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

Liquid fatty esters derived from monoalcohols will preferably be used as esters according to the invention.

Isopropyl myristate and isopropyl palmitate are particularly preferred.

The term "liquid silicone" is intended to mean an organopolysiloxane that is liquid at normal temperature (25° C.) and at atmospheric pressure (760 mmHg; i.e. $1.013 \times 10^5$ Pa).

Preferably, the silicone is chosen from liquid polydialkylsiloxanes, in particular liquid polydimethylsiloxanes (PDMS) and liquid polyorganosiloxanes comprising at least one aryl group.

These silicones may also be organomodified. The organomodified silicones that can be used in accordance with the invention are liquid silicones as defined above and comprising in their structure one or more organofunctional groups attached via a hydrocarbon-based group.

Organopolysiloxanes are defined in greater detail in the book by Walter NOLL "*Chemistry and Technology of Silicones*" (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof.

Mention may also be made of cyclocopolymers of the dimethylsiloxane/methylalkylsiloxane type, such as Volatile Silicone® FZ 3109 sold by the company Union Carbide, of formula:

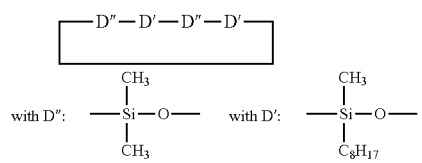

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;
(ii) linear volatile polydialkylsiloxanes containing 2 to 9 silicon atoms and having a viscosity of less than or equal to 5.10 m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, Volatile Silicone Fluids for Cosmetics. The viscosity of the silicones is measured at 25° C. according to ASTM standard 445 Appendix C.

Non-volatile polydialkylsiloxanes may also be used.

These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:
  the Silbione® oils of the 47 and 70 047 series or the Mirasil® oils sold by Rhodia, for instance the oil 70 047 V 500 000;
  the oils of the Mirasil® series sold by the company Rhodia;
  the oils of the 200 series from the company Dow Corning, such as DC200 with a viscosity of 60 000 mm$^2$/s;
  the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

Among the silicones containing aryl groups are polydiarylsiloxanes, in particular polydiphenylsiloxanes and polyalkylarylsiloxanes. Examples that may be mentioned include the products sold under the following names:
  the Silbione® oils of the 70 641 series from Rhodia;
  the oils of the Rhodorsil® 70 633 and 763 series from Rhodia;
  the oil Dow Corning 556 Cosmetic Grade Fluid from Dow Corning;
  the silicones of the PK series from Bayer, such as the product PK20;
  certain oils of the SF series from General Electric, such as SF 1023, SF 1154, SF 1250 and SF 1265.

The organomodified liquid silicones may in particular contain polyethyleneoxy and/or polypropyleneoxy groups. Mention may thus be made of the silicone KF-6017 proposed by Shin-Etsu, and the oils Silwet® L722 and L77 from the company Union Carbide.

The liquid fatty acids are preferably unsaturated and/or branched fatty acids. Mention may be made in particular of oleic acid.

The liquid fatty ethers are chosen from liquid dialkyl ethers such as dicaprylyl ether.

The fatty substances may be non-liquid at ambient temperature and at atmospheric pressure.

The term "non-liquid" is intended to mean preferably a solid compound or a compound which has a viscosity of greater than 2 Pa·s at a temperature of 25° C. and at a shear rate of 1 s$^{-1}$.

More particularly, the non-liquid fatty substances are chosen from fatty alcohols, fatty acid and/or fatty alcohol esters, non-silicone waxes, silicones or fatty ethers which are non-liquid and preferably solid.

The non-liquid fatty alcohols that are suitable for use in the invention are more particularly chosen from saturated or unsaturated, linear or branched alcohols comprising from 8 to 30 carbon atoms. Mention may be made, for example, of cetyl alcohol, stearyl alcohol and a mixture thereof (cetylstearyl alcohol).

As regards the non-liquid esters of fatty acids and/or of fatty alcohols, mention may in particular be made of solid esters derived from $C_9$-$C_{26}$ fatty acids and from $C_9$-$C_{26}$ fatty alcohols.

Among these esters, mention may be made of octyldodecyl behenate; isocetyl behenate; cetyl lactate; stearyl octanoate; octyl octanoate; cetyl octanoate; decyl oleate; myristyl stearate; octyl palmitate; octyl pelargonate; octyl stearate; alkyl myristates such as cetyl, myristyl or stearyl myristate; hexyl stearate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

Mention may in particular be made of: diethyl sebacate; diisopropyl sebacate; diisopropyl adipate; di-n-propyl adipate; dioctyl adipate; and dioctyl maleate.

Among all the additional esters mentioned above, it is preferred to use myristyl, cetyl or stearyl palmitates, alkyl myristates such as cetyl myristate, and stearyl myristyl myristate.

The (non-silicone) wax(es) is (are) chosen in particular from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the invention are especially marine waxes such as the product sold by the company Sophim under the reference M82, and polyethylene waxes or polyolefin waxes in general.

The non-liquid silicones in accordance with the invention may be present in the form of waxes, resins or gums.

Preferably, the non-liquid silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

The silicone gums that can be used in accordance with the invention are in particular polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:

- the mixtures formed from a hydroxy-terminated polydimethylsiloxane or dimethiconol (CTFA), and from a cyclic polydimethylsiloxane, also known as cyclomethicone (CTFA), such as the product Q2 1401 sold by the company Dow Corning;
- mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and a PDMS oil, such as the product SF 1236 from the company General Electric. The product SF 1236 is the mixture of a gum SE 30 defined above having a viscosity of 20 $m^2$/s and of an oil SF 96 having a viscosity of $5.10^{-6}$ $m^2$/s. This product preferably comprises 15% of gum SE 30 and 85% of an oil SF 96.

The organopolysiloxane resins that can be used in accordance with the invention are crosslinked siloxane systems containing the following units:
$R_2SiO_{2/2}$, $R_3SiO_{1/2}$, $RSiO_{3/2}$ and $SiO_{4/2}$
in which formulae:
R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate type resins sold in particular under the names X22-4914, X21-5034 and X21-5037 by the company Shin-Etsu.

Among the additional organomodified silicones, mention may be made of polyorganosiloxanes comprising:

- substituted or unsubstituted amine groups, for instance the products sold under the names Q2 8220 and Dow Corning 929 or 939 by the company Dow Corning. The substituted amine groups are in particular $C_1$-$C_4$ aminoalkyl groups;
- alkoxy groups, such as the product sold under the name Abil Wax® 2428, 2434 and 2440 by the company Goldschmidt.

The non-liquid fatty ethers are chosen from dialkyl ethers and in particular dicetyl ether and distearyl ether, alone or as a mixture.

Preferably, the compositions of the invention contain one or more fatty substances that are liquid at normal temperature (25° C.) and at atmospheric pressure (760 mm Hg; i.e. 1.013×$10^5$ Pa), optionally combined with one or more fatty substances that are non-liquid under the same conditions.

Preferably, the fatty substance is chosen from oils of plant origin, liquid petroleum jelly, linear or branched $C_6$-$C_{16}$ lower alkanes, liquid esters and liquid fatty alcohols. Even more preferentially, the fatty substance is chosen from oils of plant origin.

When it comprises fatty substance, the composition comprises from 0.1 to 30% by weight of fatty substance, preferably from 0.5 to 20%, more preferably from 1 to 15%, relative to the total weight of the composition.

The composition may comprise one or more solvents. These solvents may be chosen from water, $C_1$-$C_4$ alcohols, such as ethanol, isopropanol, tert-butanol, n-butanol, propylene carbonate, polyols such as propylene glycol, glycerol and polyol ethers, acetone, benzyl alcohol, and mixtures thereof.

Preferably, the composition is aqueous or aqueous-alcoholic, the preferred solvent being water.

The composition according to the invention may also comprise one or more surfactants. The surfactant(s) which can be used in the composition according to the invention can be chosen from cationic, anionic, non-ionic, amphoteric or zwitterionic non-silicone surfactants, silicone surfactants and mixtures thereof.

When a surfactant is present in the composition according to the invention, said composition preferably comprises at least 0.01% by weight of surfactant(s), relative to the total weight of the composition. Preferably, the composition according to the invention comprises from 0.05 to 20% by weight of surfactant(s), more preferably from 0.1 to 10% by weight and even more preferably from 0.5 to 5% by weight, relative to the total weight of the composition.

When the composition comprises at least one fatty substance, the composition according to the invention may also contain one or more thickeners, which can be chosen from natural or synthetic, anionic, amphoteric, zwitterionic, non-ionic or cationic and associative or non-associative polymeric thickeners, and non-polymeric thickeners such as, for example, an electrolyte or a sugar.

Mention may be made, as polymeric thickeners, for example, of cellulosic thickeners, for example hydroxyethylcellulose, hydroxypropylcellulose and carboxymethylcellulose, guar gum and its derivatives, for example hydroxypropyl guar, sold by the company Rhodia under the reference Jaguar HP 105, gums of microbial origin, such as xanthan gum and scleroglucan gum, synthetic polymeric thickeners, such as crosslinked homopolymers of acrylic acid or of acrylamidopropanesulphonic acid, for example Carbomer, or non-ionic, anionic or amphoteric associative polymers, such as the polymers sold under the names Pemulen TR1 or TR2 by the company Goodrich, Salcare SC90 by the company Allied Colloids, Aculyn 22, 28, 33, 44 or 46 by the company Rohm & Haas and Elfacos T210 and T212 by the company Akzo.

The composition according to the invention can also comprise one or more plasticizers.

The composition of the invention may also contain one or more fixing polymers. For the purpose of the invention, the term "fixing polymer" is intended to mean any polymer which makes it possible to shape or retain the shape of the hair.

The composition used in the process of the invention has a pH ranging from 3 to 8, preferably from 3 to 5, even more preferentially from 3 to 4.

The composition may comprise pH adjusters other than the carboxylic acids of the invention. The pH adjusters may be acidifying or basifying agents.

Among the acidifying agents, mention may be made, by way of example, of mineral or organic acids, such as hydrochloric acid, orthophosphoric acid, sulphuric acid, or sulphonic acids.

Mention may be made, among the basifying agents, by way of example, of aqueous ammonia, alkaline carbonates, alkanolamines, such as mono-, di- and triethanolamines, and their derivatives, sodium hydroxide, potassium hydroxide and the compounds with the following formula:

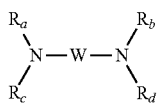

in which W is a propylene residue optionally substituted with a hydroxyl group or a $C_1$-$C_4$ alkyl radical; $R_a$, $R_b$, $R_c$ and $R_d$, which are identical or different, represent a hydrogen atom or a $C_1$-$C_4$ alkyl or $C_1$-$C_4$ hydroxyalkyl radical.

Preferably, the pH adjusters can be chosen from alkaline agents, such as aqueous ammonia, monoethanolamine, diethanolamine, triethanolamine, 1,3-propanediamine or an alkaline hydroxide, such as 2-amino-2-methyl-1-propanol, or else acidifying agents, such as phosphoric acid or hydrochloric acid.

The composition of the invention may be in the form of a foam, a gel, a serum, a liquid lotion or a lacquer.

The composition may be packaged in a pump-dispenser bottle or in an aerosol device.

When it is packaged in an aerosol-type device, the liquid phase/propellant weight ratio of the pressurized composition of the present invention is preferably from 50 to 0.05, and in particular from 50 to 1.

For the aerosol formulations, any halogenated or non-halogenated, volatile alkane which is customarily used in aerosol devices will be used as propellant gas.

Preferably, the compound(s) constituting the propellant is (are) chosen from non-halogenated $C_3$-$C_5$ alkanes, such as propane, n-butane and isobutane, halogenated, and in particular chlorinated and/or fluorinated, $C_3$-$C_5$ alkanes, such as 1,1-difluoroethane, and mixtures thereof.

According to a particularly preferred embodiment, said alkane(s) of the propellant gas is (are) non-halogenated. Even more preferably, the propellant gas is a mixture of propane, n-butane and isobutane.

In the case of aerosol foams, the composition introduced into the aerosol device may, for example, be in the form of a lotion, or dispersions or emulsions which, after dispensing from the aerosol device, form foams to be applied to keratin substances.

These foams must be sufficiently stable not to rapidly liquefy and must also rapidly disappear, either spontaneously or during the massaging which is used to cause the composition to penetrate into keratin substances and/or to distribute the composition over keratin substances and more particularly the head of hair and/or the hair.

For the aerosol formulations, the propellant may be any liquefiable gas customarily used in aerosol devices. Dimethyl ether, $C_3$-$C_5$ alkanes, chlorinated and/or fluorinated hydrocarbons such as 1,1-difluoroethane, and mixtures thereof, for instance mixtures of dimethyl ether and of $C_3$-$C_5$ alkanes, and mixtures of 1,1-difluoroethane and of dimethyl ether and/or of $C_3$-$C_5$ alkanes, are in particular chosen. Carbon dioxide, nitrous oxide, nitrogen or compressed air, or mixtures thereof, may also be used as propellant.

Preferably, the propellant gas used is dimethyl ether or $C_3$-$C_5$ alkanes, and in particular propane, n-butane and isobutane, and mixtures thereof.

The propellant gas is present in the compositions according to the invention in proportions preferably ranging from 1 to 99% by weight, more preferentially from 1.5 to 50% by weight and better still from 2 to 30% by weight, relative to the total weight of the composition.

The aerosol device used to package the composition of the invention may be made up of two compartments, formed from an outer aerosol can comprising an inner bag hermetically sealed to a valve. The composition is introduced into the inner bag and a compressed gas is introduced between the bag and the can at a pressure sufficient to make the product come out in the form of a spray through a nozzle orifice. Such a device is sold, for example, under the name EP Spray by the company EP-Spray System SA. Said compressed gas is preferably used at a pressure of from 1 to 12 bar and even better still from 9 to 11 bar.

The composition according to the invention can be applied at ambient temperature or with a contribution of heat, for example using a hairdryer, a hood or a smoothing iron of flat tongs.

The composition according to the invention may also contain one or more adjuvants chosen from cellulosic polymers, ceramides and pseudoceramides, vitamins and pro-vitamins, including panthenol, silicone or non-silicone sunscreens, pearlescent agents and opacifiers, sequestering agents, conditioning agents, solubilizing agents, antioxidants, penetrating agents, fragrances, peptizers, preservatives, direct and oxidation dyes, organic or mineral pigments, agents for long-lasting shaping of the hair (thiol organic reducing agents, non-thiol organic reducing agents, alkaline agents, etc), and any other additive conventionally used in the cosmetics field.

A person skilled in the art will take care to choose the optional additives and amounts thereof so that they do not interfere with the properties of the compositions of the present invention. These additives may be present in the composition according to the invention in an amount ranging from 0 to 20% by weight relative to the total weight of the composition.

According to the invention, a composition comprising at least one carboxylic acid in its acid or salified form, at a concentration greater than or equal to 2%, and at least one non-cellulosic polymer, the pH ranging from 3 to 8, is applied to straightened hair at ambient temperature (preferably at a temperature between 22 and 27° C.).

In a preferred variant, the straightened hair was straightened beforehand using a hair-straightening composition containing an alkaline agent, in particular sodium hydroxide or guanidine. The hair-straightening composition containing an alkaline agent may be any professional or public commercial hair-straightening agent based on sodium hydroxide or guanidine (Dark and Lovely or Soft Sheen Carson are the preferred hair-straightening agents). They may be of different strengths: resistant hair (strong), slightly sensitized hair (regular) or very sensitized hair (mild).

After the hair-straightening, the hair is rinsed with water and optionally washed with a shampoo.

The composition for treating straightened hair is then applied to wet or dry hair. The composition is preferably applied to wet hair. When it is applied to dry hair, the hair has been dried with a hairdryer or with a hood or air-dried.

The composition is left on the hair for a period of time ranging from 5 min to 2 hours, preferably for a period of time ranging from 5 to 30 min, preferably for a period of time ranging from 10 to 30 min, more preferably for approximately 20 min. During the leave-on time of the treatment, the hair may optionally be covered with a towel, a scarf, or any other covering, and heat may optionally be maintained on the hair by means of a hood or a hairdryer.

The hair may subsequently be rinsed and then washed with a shampoo. The hair is subsequently dried with a hairdryer or a hood or air-dried.

Another care treatment may be applied before or after the composition according to the invention.

The process according to the invention may also comprise a step of smoothing the hair with a smoothing iron. The smoothing iron is preferentially passed over semi-dry hair at the end of treatment in order to finalize the aesthetic quality of the hairstyle.

The application can be repeated as many times as necessary following hair-straightening, after each shampooing procedure, each day, or only after each hair-straightening treatment.

Concrete examples illustrating the invention will now be given.

inorganic acid replacing the composition of example 2. The hair-straightening quality obtained with the composition of example 6 is identical to that obtained with the composition of example 8 without hydrochloric acid. The application of the composition of example 6 does not improve the hair-straightening effectiveness compared with the same composition without hydrochloric acid, whereas composition 2 under the same conditions enables, compared with composition 6, a reduction in volume, a better feel and persistence of the hair-straightening.

TABLE 1

| Composition | Ex. 1 | Ex. 2 | Ex. 3 | Ex. 4 | Ex. 5 | Ex. 6 | Ex. 7 | Ex. 8 Control |
|---|---|---|---|---|---|---|---|---|
| Citric acid | 2 | — | — | — | — | — | — | — |
| Sodium citrate | — | 2 | — | — | — | — | — | — |
| Aspartic acid | — | — | 5 | — | — | — | — | — |
| Sodium succinate | — | — | — | 5 | — | — | — | — |
| X*** | — | — | — | — | 5 | — | — | — |
| Hydrochloric acid | — | — | — | — | — | 2 | — | — |
| Phosphoric acid | — | — | — | — | — | — | 2 | — |
| Benzyl alcohol | 0.5 | 2 | 4 | 4 | 4 | 2 | — | 2 |
| Polystyrene in an emulsion in water at 40% (Modarez OS 197)* | 0.12 | 0.12 | — | 0.12 | — | 0.12 | 0.12 | 0.12 |
| Rheolate FX 1100** | — | 2.5 | 2.5 | — | 2.5 | 2.5 | 2.5 | 2.5 |
| Preservatives | 1.3 | 1.3 | 1.3 | 1.3 | 1.3 | 1.3 | 1.3 | 1.3 |
| Castor oil | 1.6 | 1.6 | 1.6 | 1.6 | 1.6 | 1.6 | 1.6 | 1.6 |
| pH adjuster if necessary (sodium hydroxide or hydrochloric acid) | qs pH 3.5 | spontaneous pH | qs pH 3.5 | qs pH 7 | qs pH 7 | spontaneous pH | spontaneous pH | spontaneous pH |
| Water | qs | qs | qs | qs | qs | qs | qs | qs |

*sold by Synthron
**sold by Elementis, polyoxyethylenated polyurethane polyether comprising an alpha, omega stearyl end group, Rheolate FX 1100
***X: acids tested: maleic acid, sodium maleate, succinic acid, sodium aspartate, glutamic acid, sodium glutamate, lactic acid, sodium lactate, malic acid, sodium malate, tartaric acid, sodium tartrate.

An entire head of frizzy hair of afro type is treated with an alkaline hair-straightening product containing guanidine, sold under the name Dark and Lovely Moisture System No-lye, regular, with a leave-on time of 20 minutes. The hair-straightening treatment is rinsed off with water.

The composition of example 2 is applied to half a head, the composition being in the form of a serum or a cream. The composition of example 8, which is identical to the composition of example 2, but which does not comprise sodium citrate, is applied to the other half of the head. It is left on for 20 minutes. The hair is then partially dried with a hairdryer for 5 minutes. A smoothing iron is passed over each lock twice, over the whole of the head of hair.

A clear difference is then observed between the treatment comprising the composition of example 2 and the treatment comprising the composition of example 8 without sodium citrate: the hair is more flattened against the roots, much less voluminous overall, and has a more pleasant feel, without rough patches, after treatment with the composition of example 2.

The same protocol is applied to a head of hair of the same type, with the composition of example 6 which contains an

TABLE 2

| Composition | Ex. 2.1 | Ex. 2.2 | Ex. 2.3 | Ex. 2.4 | Ex. 2.5 Control |
|---|---|---|---|---|---|
| Citric acid | 2 | — | — | — | — |
| Sodium citrate | — | 2 | — | — | — |
| Hydrochloric acid | — | — | 2 | — | — |
| Phosphoric acid | — | — | — | 2 | — |
| Mixture of oxyethylenated oxypropylenated polydimethylsiloxane (18EO/18PO), of decamethylcyclopentasiloxane and of water (10/88/2) * | 15 | 15 | 15 | 15 | 15 |
| Preservatives | 1.3 | 1.3 | 1.3 | 1.3 | 1.3 |
| Castor oil | 1.6 | 1.6 | 1.6 | 1.6 | 1.6 |
| pH adjuster if necessary (sodium hydroxide or hydrochloric acid) | qs pH 3.5 | spontaneous pH | spontaneous pH | spontaneous pH | spontaneous pH |
| Water | qs | qs | qs | qs | qs |

* PEG/PPG-18/18 Dimethicone sold by Dow Corning under the commercial reference 5225C.

An entire head of frizzy hair of afro type is treated with an alkaline hair-straightening product containing guanidine, sold under the name Dark and Lovely Moisture System No-lye, regular, with a leave-on time of 20 minutes. The hair-straightening treatment is rinsed off with water.

The composition of example 2.2 is applied to half a head. The composition of example 2.5, which does not comprise sodium citrate, is applied to the other half of the head. It is left on for 20 minutes. The hair is then partially dried with a hairdryer for 5 minutes. A smoothing iron is passed over each lock twice, over the whole of the head of hair.

A clear difference in result is then observed between the treatment comprising the composition of example 2.2 and the treatment with the composition of example 2.5: the hair treated with the composition of example 2.2 is more flattened against the roots, much less voluminous overall, and has a more pleasant feel, without rough patches.

The same protocol is applied to a head of hair of the same type, with the composition of example 2.3 which contains an inorganic acid replacing the composition of example 2.2. The hair-straightening quality obtained with the composition of example 2.3 is identical to that obtained with the composition of example 2.5. The application of the composition of example 2.3 does not improve the hair-straightening effectiveness compared with the application of the same composition without hydrochloric acid.

The composition of example 2.2 is applied to half a head. The composition of example 2.3, which does not comprise sodium citrate but an inorganic acid, is applied to the other half of the head. It is left on for 20 minutes. The hair is then partially dried with a hairdryer for 5 minutes. A smoothing iron is passed over each lock twice, over the whole of the head of hair.

A clear difference in results is then observed between the treatment comprising the composition of example 2.2 and the treatment with the composition of example 2.3: the hair treated with the composition of example 2.2 is more flattened against the roots, much less voluminous overall, and has a more pleasant feel, without rough patches.

Other compositions can be prepared according to the following examples, the data in the table being expressed as percentages by weight of active material in the final composition.

| Composition | Ex. 2.6 | Ex. 2.7 | Ex. 2.8 |
|---|---|---|---|
| Aspartic acid | 5 | — | — |
| Sodium succinate | — | 5 | — |
| Maleic acid | — | — | 5 |
| Mixture of oxyethylenated oxypropylenated polydimethylsiloxane (18EO/18PO), of decamethylcyclopentasiloxane and of water (10/88/2) * | 15 | 15 | 15 |
| Preservatives | 1.3 | 1.3 | 1.3 |
| Castor oil | 1.6 | 1.6 | 1.6 |
| pH adjuster if necessary (sodium hydroxide or hydrochloric acid) | qs pH 3.5 | qs pH 7 | qs pH 7 |
| Water | qs | qs | qs |

* PEG/PPG-18/18 Dimethicone sold by Dow Corning under the commercial reference 5225C Other compositions may also be prepared by replacing, in example 2.8, the maleic acid with, respectively, sodium maleate, succinic acid, sodium aspartate, glutamic acid, sodium glutamate, lactic acid, sodium lactate, malic acid, sodium malate, tartaric acid and sodium tartrate.

The invention claimed is:

1. A process for treating straightened keratin fibers, said process comprising a step of:
   applying to the straightened keratin fibers a composition comprising:
   at least one carboxylic acid in its acid or salified form, at a concentration of greater than or equal to about 2%, and
   at least one component chosen from non-cellulosic polymers and fatty substances,
   wherein the pH of the composition ranges from about 3 to about 7.

2. The process according to claim 1, wherein the composition comprises at least one carboxylic acid chosen from tricarboxylic acids or salts thereof, dicarboxylic acids or salts thereof, amino dicarboxylic acids or salts thereof, monocarboxylic acids or salts thereof, α-hydroxylated carboxylic acids or salts thereof, and dihydroxylated carboxylic acids or salts thereof.

3. The process according to claim 1, wherein the composition comprises at least one carboxylic acid or one carboxylic acid salt chosen from citric acid, sodium citrate, maleic acid, sodium maleate, succinic acid, sodium succinate, aspartic acid, sodium aspartate, glutamic acid, sodium glutamate, lactic acid, sodium lactate, malic acid, sodium malate, tartaric acid and sodium tartrate.

4. The process according to claim 1, wherein the carboxylic acid is chosen from citric acid and salts thereof.

5. The process according to claim 1, wherein the composition comprises carboxylic acid in acid or salified form in an amount ranging from about 2% to about 50%.

6. The process according to claim 1, wherein the composition comprises carboxylic acid in acid or salified form in an amount ranging from about 2% to about 5%.

7. The process according to claim 1, wherein the non-cellulosic polymers are chosen from non-ionic, anionic, cationic, amphoteric and zwitterionic polymers, which are soluble or insoluble in the composition.

8. The process according to claim 1, wherein the non-cellulosic polymers are chosen from thickening polymers, fixing polymers, opacifying polymers, conditioning polymers, and mixtures thereof.

9. The process according to claim 1, wherein the non-cellulosic polymers are chosen from homopolymers and copolymers containing at least one ethylenically unsaturated monomer, polysaccharides, optionally modified guar gums, optionally modified xanthan gums, polyurethanes, and mixtures thereof.

10. The process according to claim 1, wherein the composition comprises from about 0.01% to about 50% of one or more non-cellulosic polymers, relative to the total weight of the composition.

11. The process according to claim 1, wherein the composition comprises from about 1% to about 5% of one or more non-cellulosic polymers, relative to the total weight of the composition.

12. The process according to claim 1, wherein the fatty substances are chosen from fatty substances that are liquid at ambient temperature, defined as about 25° C. and at atmospheric pressure, defined as about 760 mmHg or about $1.013 \times 10^5$ Pa.

13. The process according to claim 1, wherein the fatty substances are chosen from hydrocarbons, fatty alcohols, fatty esters, silicones, fatty ethers, and mixtures thereof.

14. The process according to claim 1, wherein the fatty substances are chosen from oils of plant origin, liquid petroleum jelly, linear or branched $C_6$-$C_{16}$ lower alkanes, liquid esters, liquid fatty alcohols, and mixtures thereof.

15. The process according to claim 1, wherein the composition comprises from about 0.1% to about 30% of at least one fatty substance.

16. The process according to claim 1, wherein the composition comprises from about 1% to about 15% of at least one fatty substance.

17. The process according to claim 1, wherein the composition has a pH ranging from about 3 to about 4.

18. The process according to claim 1, further comprising leaving the composition on the keratin fibers for a period of time ranging from about 5 minutes to about 2 hours.

19. The process according to claim 1, further comprising leaving the composition on the keratin fibers for about 20 minutes.

20. The process according to claim 1, wherein the keratin fibers have been straightened beforehand by applying a composition comprising an alkaline hydroxide.

21. The process according to claim 1, wherein the composition is applied to wet hair.

22. The process according to claim 1, further comprising smoothing the hair with a smoothing iron.

23. The process according to claim 1, wherein the treating is chosen from reducing hair volume and increasing the persistence of hair-straightening.

\* \* \* \* \*